(12) United States Patent
Wheeler et al.

(10) Patent No.: US 11,833,515 B2
(45) Date of Patent: Dec. 5, 2023

(54) MICROFLUIDIC CHANNEL NETWORKS FOR PARTITIONING

(71) Applicant: 10x Genomics, Inc., Pleasanton, CA (US)

(72) Inventors: Tobias Daniel Wheeler, Pleasanton, CA (US); Bill Kengli Lin, Pleasanton, CA (US); Mohammad Rahimi Lenji, Livermore, CA (US); Anthony Makarewicz, Livermore, CA (US); Rajiv Bharadwaj, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 689 days.

(21) Appl. No.: 16/859,060

(22) Filed: Apr. 27, 2020

(65) Prior Publication Data

US 2020/0391211 A1    Dec. 17, 2020

Related U.S. Application Data

(63) Continuation of application No. PCT/US2018/056766, filed on Oct. 19, 2018.

(60) Provisional application No. 62/577,402, filed on Oct. 26, 2017.

(51) Int. Cl.
*B01L 3/00* (2006.01)
*C12Q 1/6869* (2018.01)

(52) U.S. Cl.
CPC ... *B01L 3/502784* (2013.01); *B01L 3/502761* (2013.01); *C12Q 1/6869* (2013.01); *B01L 2200/06* (2013.01); *B01L 2200/16* (2013.01); *B01L 2300/021* (2013.01); *B01L 2300/0861* (2013.01)

(58) Field of Classification Search
CPC ......... B01L 3/502784; B01L 3/502761; B01L 2200/06; B01L 2200/16; B01L 2300/021; B01L 2300/0861; B01L 2200/0673; B01L 2400/0487; B01L 3/0241; C12Q 1/6869; C12M 25/01
See application file for complete search history.

(56) References Cited

U.S. PATENT DOCUMENTS

| | | | |
|---|---|---|---|
| 5,700,692 A | 12/1997 | Sweet | |
| 5,837,200 A | 11/1998 | Diessel et al. | |
| 6,057,149 A | 5/2000 | Burns et al. | |
| 6,123,798 A | 9/2000 | Gandhi et al. | |
| 6,176,962 B1 | 1/2001 | Soane et al. | |
| 6,177,479 B1 | 1/2001 | Nakajima et al. | |
| 6,281,018 B1 | 8/2001 | Kirouac et al. | |
| 6,328,421 B1 | 12/2001 | Kojima et al. | |
| 6,778,724 B2 | 8/2004 | Wang et al. | |
| 6,808,075 B2 | 10/2004 | Bohm et al. | |
| 6,877,528 B2 | 4/2005 | Gilbert et al. | |
| 6,915,679 B2 | 7/2005 | Chien et al. | |
| 6,976,590 B2 | 12/2005 | Deshpande et al. | |
| 6,994,218 B2 | 2/2006 | Kawano et al. | |
| 7,104,405 B2 | 9/2006 | Bohm et al. | |
| 7,241,988 B2 | 7/2007 | Gruber et al. | |
| 7,264,972 B2 | 9/2007 | Foster | |
| 7,452,725 B2 | 11/2008 | Leary et al. | |
| 7,569,788 B2 | 8/2009 | Deshpande et al. | |
| 7,584,857 B2 | 9/2009 | Bohm et al. | |
| 7,622,076 B2 | 11/2009 | Davies et al. | |
| 7,699,767 B2 | 4/2010 | Mueth et al. | |
| 7,704,395 B2 | 4/2010 | Mueth et al. | |
| 7,723,116 B2 | 5/2010 | Evans et al. | |
| 7,767,444 B2 | 8/2010 | Liu et al. | |
| 7,772,287 B2 | 8/2010 | Higuchi et al. | |
| 7,901,947 B2 | 3/2011 | Pollack et al. | |
| 7,927,797 B2 | 4/2011 | Nobile et al. | |
| 7,943,671 B2 | 5/2011 | Herminghaus et al. | |
| 7,963,399 B2 | 6/2011 | Bohm et al. | |
| 8,029,744 B2 | 10/2011 | Noda et al. | |
| 8,096,421 B2 | 1/2012 | Shinoda | |
| 8,186,913 B2 | 5/2012 | Toner et al. | |
| 8,198,092 B2 | 6/2012 | Durack et al. | |
| 8,241,914 B2 | 8/2012 | Durack et al. | |
| 8,246,805 B2 | 8/2012 | Shinoda | |
| 8,298,767 B2 | 10/2012 | Brenner et al. | |
| 8,387,803 B2 | 3/2013 | Thorslund et al. | |
| 8,408,399 B2 | 4/2013 | Bohm et al. | |
| 8,454,906 B2 | 6/2013 | Mathies et al. | |
| 8,467,040 B2 | 6/2013 | Luscher | |
| 8,524,173 B2 | 9/2013 | Yamanaka et al. | |
| 8,529,026 B2 | 9/2013 | Clarke et al. | |

(Continued)

FOREIGN PATENT DOCUMENTS

| | | | |
|---|---|---|---|
| EP | 1684078 A2 | 7/2006 | |
| GB | 2097692 A | 11/1982 | |

(Continued)

OTHER PUBLICATIONS

Abate et al., "Beating Poisson encapsulation statistics using close-packed ordering," Lab Chip. 9(18):2628-31 (2009).
Abate et al., "High-throughput injection with microfluidics using picoinjectors," Proc Natl Acad Sci U S A. 107(45): 19163-6 (2010).
Abate et al., "Valve based flow focusing for drop formation," Appl Phys Lett. 94(2):023503-1-3 (2009) (3 pages).
AGC Chemicals, "Amorphous Fluoropolymer CYTOP:Chemistry for a Blue Planet," Jul. 2015 (10 pages).
AGC Chemicals, "Water/oil-repellent fluororesin coating material CYTOP(TM)," 2015 (1 page).

(Continued)

*Primary Examiner* — Narayan K Bhat
(74) *Attorney, Agent, or Firm* — Clark & Elbing LLP

(57) ABSTRACT

Provided are microfluidics systems, devices, and networks for generating partitions. The microfluidics systems, devices, and networks may facilitate efficient merging of one or more channels in a microfluidic network and prevent blockage of a channel segment, such as by gas (e.g., air) bubbles or by one or more particles in a fluid.

10 Claims, 16 Drawing Sheets

(56) References Cited

U.S. PATENT DOCUMENTS

| | | |
|---|---|---|
| 8,563,274 B2 | 10/2013 | Brenner et al. |
| 8,567,608 B2 | 10/2013 | Deshpande et al. |
| 8,592,221 B2 | 11/2013 | Fraden et al. |
| 8,609,422 B2 | 12/2013 | Durack et al. |
| 8,613,890 B2 | 12/2013 | Muraki |
| 8,633,015 B2 | 1/2014 | Ness et al. |
| 8,658,368 B2 | 2/2014 | Quake et al. |
| 8,658,430 B2 | 2/2014 | Miller et al. |
| 8,679,756 B1 | 3/2014 | Brenner et al. |
| 8,741,192 B2 | 6/2014 | Torii et al. |
| 8,795,500 B2 | 8/2014 | Shinoda |
| 8,807,879 B2 | 8/2014 | Toner et al. |
| 8,820,538 B1 | 9/2014 | Lin |
| 8,821,006 B2 | 9/2014 | Norikane et al. |
| 8,857,462 B2 | 10/2014 | Miller et al. |
| 8,871,500 B2 | 10/2014 | Foster et al. |
| 8,944,083 B2 | 2/2015 | Collier et al. |
| 8,986,628 B2 | 3/2015 | Stone et al. |
| 9,012,390 B2 | 4/2015 | Holtze et al. |
| 9,017,623 B2 | 4/2015 | Fraden et al. |
| 9,089,844 B2 | 7/2015 | Hiddessen et al. |
| 9,102,980 B2 | 8/2015 | Brenner et al. |
| 9,108,173 B2 | 8/2015 | Lee et al. |
| 9,126,160 B2 | 9/2015 | Ness et al. |
| 9,132,394 B2 | 9/2015 | Makarewicz, Jr. et al. |
| 9,133,009 B2 | 9/2015 | Baroud et al. |
| 9,156,010 B2 | 10/2015 | Colston, Jr. et al. |
| 9,194,861 B2 | 11/2015 | Hindson et al. |
| 9,207,160 B2 | 12/2015 | Shinoda |
| 9,216,392 B2 | 12/2015 | Hindson et al. |
| 9,248,417 B2 | 2/2016 | Hindson et al. |
| 9,266,104 B2 | 2/2016 | Link |
| 9,273,308 B2 | 3/2016 | Link et al. |
| 9,328,376 B2 | 5/2016 | Hiddessen et al. |
| 9,339,850 B2 | 5/2016 | Deshpande et al. |
| 9,388,465 B2 | 7/2016 | Hindson et al. |
| 9,393,560 B2 | 7/2016 | Ness et al. |
| 9,399,215 B2 | 7/2016 | Cauley, III et al. |
| 9,403,294 B2 | 8/2016 | Cauley, III |
| 9,409,174 B2 | 8/2016 | Makarewicz, Jr. et al. |
| 9,410,149 B2 | 8/2016 | Brenner et al. |
| 9,410,150 B2 | 8/2016 | Brenner et al. |
| 9,410,201 B2 | 8/2016 | Hindson et al. |
| 9,417,190 B2 | 8/2016 | Hindson et al. |
| 9,427,737 B2 | 8/2016 | Heredia et al. |
| 9,486,757 B2 | 11/2016 | Romanowsky et al. |
| 9,492,797 B2 | 11/2016 | Makarewicz et al. |
| 9,500,664 B2 | 11/2016 | Ness et al. |
| 9,527,049 B2 | 12/2016 | Hiddessen et al. |
| 9,562,837 B2 | 2/2017 | Link |
| 9,567,631 B2 | 2/2017 | Hindson et al. |
| 9,623,384 B2 | 4/2017 | Hindson et al. |
| 9,638,620 B2 | 5/2017 | Di Carlo et al. |
| 9,644,204 B2 | 5/2017 | Hindson et al. |
| 9,683,792 B2 | 6/2017 | Possinger et al. |
| 9,687,848 B2 | 6/2017 | Makarewicz, Jr. et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,700,891 B2 | 7/2017 | Smith et al. |
| 9,701,998 B2 | 7/2017 | Hindson et al. |
| 9,702,808 B2 | 7/2017 | Lin |
| 9,764,322 B2 | 9/2017 | Hiddessen et al. |
| 9,824,068 B2 | 11/2017 | Wong |
| 9,856,530 B2 | 1/2018 | Hindson et al. |
| 9,896,722 B2 | 2/2018 | Link |
| 9,946,577 B1 | 4/2018 | Stafford et al. |
| 9,951,386 B2 | 4/2018 | Hindson et al. |
| 9,975,122 B2 | 5/2018 | Masquelier et al. |
| 10,071,377 B2 | 9/2018 | Bharadwaj et al. |
| 10,137,449 B2 | 11/2018 | Bharadwaj et al. |
| 10,150,117 B2 | 12/2018 | Bharadwaj et al. |
| 10,343,166 B2 | 7/2019 | Bharadwaj et al. |
| 10,357,771 B2 | 7/2019 | Bharadwaj et al. |
| 10,544,413 B2 | 1/2020 | Bharadwaj et al. |
| 10,549,279 B2 | 2/2020 | Bharadwaj et al. |
| 10,583,440 B2 | 3/2020 | Bharadwaj et al. |
| 10,610,865 B2 | 4/2020 | Bharadwaj et al. |
| 10,688,494 B2 | 6/2020 | Bharadwaj et al. |
| 10,697,000 B2 | 6/2020 | Belgrader et al. |
| 10,766,032 B2 | 9/2020 | Bharadwaj et al. |
| 10,821,442 B2 | 11/2020 | Bharadwaj et al. |
| 10,898,900 B2 | 1/2021 | Bharadwaj et al. |
| 2002/0058332 A1 | 5/2002 | Quake et al. |
| 2002/0127736 A1 | 9/2002 | Chou et al. |
| 2003/0228610 A1 | 12/2003 | Seul |
| 2004/0068019 A1 | 4/2004 | Higuchi et al. |
| 2004/0109793 A1 | 6/2004 | McNeely et al. |
| 2005/0103690 A1 | 5/2005 | Kawano et al. |
| 2005/0249636 A1 | 11/2005 | Tacklind et al. |
| 2005/0266582 A1 | 12/2005 | Modlin et al. |
| 2006/0078888 A1 | 4/2006 | Griffiths et al. |
| 2006/0078893 A1 | 4/2006 | Griffiths et al. |
| 2007/0065808 A1 | 3/2007 | Bohm et al. |
| 2007/0117086 A1 | 5/2007 | Evans et al. |
| 2007/0166200 A1 | 7/2007 | Zhou et al. |
| 2007/0196397 A1 | 8/2007 | Torii et al. |
| 2008/0003142 A1 | 1/2008 | Link et al. |
| 2008/0038810 A1 | 2/2008 | Pollack et al. |
| 2008/0050283 A1 | 2/2008 | Chou et al. |
| 2008/0053205 A1 | 3/2008 | Pollack et al. |
| 2008/0056948 A1 | 3/2008 | Dale et al. |
| 2008/0138876 A1 | 6/2008 | Ragsdale |
| 2008/0166720 A1 | 7/2008 | Hsieh et al. |
| 2008/0295909 A1 | 12/2008 | Locascio et al. |
| 2009/0012187 A1 | 1/2009 | Chu et al. |
| 2009/0035770 A1 | 2/2009 | Mathies et al. |
| 2009/0047713 A1 | 2/2009 | Handique |
| 2009/0131543 A1 | 5/2009 | Weitz et al. |
| 2009/0155563 A1 | 6/2009 | Petsev et al. |
| 2009/0235990 A1 | 9/2009 | Beer |
| 2009/0269248 A1 | 10/2009 | Falb et al. |
| 2009/0269824 A1 | 10/2009 | Kim et al. |
| 2009/0325217 A1 | 12/2009 | Luscher |
| 2010/0006441 A1 | 1/2010 | Renaud et al. |
| 2010/0018584 A1 | 1/2010 | Bransky et al. |
| 2010/0022414 A1 | 1/2010 | Link et al. |
| 2010/0022680 A1 | 1/2010 | Karnik et al. |
| 2010/0105866 A1 | 4/2010 | Fraden et al. |
| 2010/0163109 A1 | 7/2010 | Fraden et al. |
| 2010/0184928 A1 | 7/2010 | Kumacheva |
| 2010/0216208 A1 | 8/2010 | Mueth et al. |
| 2011/0005978 A1 | 1/2011 | Bohm et al. |
| 2011/0053798 A1 | 3/2011 | Hindson et al. |
| 2011/0086377 A1 | 4/2011 | Thwar et al. |
| 2011/0223314 A1 | 9/2011 | Zhang et al. |
| 2011/0267457 A1 | 11/2011 | Weitz et al. |
| 2012/0015382 A1 | 1/2012 | Weitz et al. |
| 2012/0091059 A1 | 4/2012 | Beer et al. |
| 2012/0121480 A1 | 5/2012 | Frenz et al. |
| 2012/0122714 A1 | 5/2012 | Samuels et al. |
| 2012/0142018 A1 | 6/2012 | Jiang |
| 2012/0196288 A1 | 8/2012 | Beer |
| 2012/0199226 A1 | 8/2012 | Weitz et al. |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0222748 A1 | 9/2012 | Weitz et al. |
| 2012/0231444 A1 | 9/2012 | Quake et al. |
| 2012/0236299 A1 | 9/2012 | Chiou et al. |
| 2012/0301869 A1 | 11/2012 | Evans |
| 2012/0315690 A1 | 12/2012 | Di Carlo et al. |
| 2013/0046030 A1 | 2/2013 | Rotem et al. |
| 2013/0059310 A1 | 3/2013 | Brenner et al. |
| 2013/0064776 A1 | 3/2013 | El Harrak et al. |
| 2013/0084572 A1 | 4/2013 | Hindson et al. |
| 2013/0109575 A1 | 5/2013 | Kleinschmidt et al. |
| 2013/0130919 A1 | 5/2013 | Chen et al. |
| 2013/0146461 A1 | 6/2013 | Pamula et al. |
| 2013/0149737 A1 | 6/2013 | Seidel et al. |
| 2013/0203172 A1 | 8/2013 | Wex et al. |
| 2013/0236901 A1 | 9/2013 | Potier et al. |
| 2013/0260447 A1 | 10/2013 | Link |
| 2013/0281316 A1 | 10/2013 | Ismagilov et al. |

(56) References Cited

U.S. PATENT DOCUMENTS

| | | |
|---|---|---|
| 2013/0337575 A1 | 12/2013 | Fox et al. |
| 2014/0024023 A1 | 1/2014 | Cauley, III et al. |
| 2014/0080226 A1 | 3/2014 | Cauley, III et al. |
| 2014/0087412 A1 | 3/2014 | Fouras et al. |
| 2014/0155295 A1 | 6/2014 | Hindson et al. |
| 2014/0161685 A1 | 6/2014 | Lee et al. |
| 2014/0179544 A1 | 6/2014 | Steenblock et al. |
| 2014/0199730 A1 | 7/2014 | Agresti et al. |
| 2014/0220350 A1 | 8/2014 | Kim et al. |
| 2014/0221239 A1 | 8/2014 | Carman et al. |
| 2014/0235506 A1 | 8/2014 | Hindson et al. |
| 2014/0272996 A1 | 9/2014 | Bemis |
| 2014/0273198 A1 | 9/2014 | Saito et al. |
| 2014/0273201 A1 | 9/2014 | Saito et al. |
| 2014/0273202 A1 | 9/2014 | Saito et al. |
| 2014/0287963 A1 | 9/2014 | Hindson et al. |
| 2014/0312534 A1 | 10/2014 | Cauley, III |
| 2014/0326339 A1 | 11/2014 | Toner et al. |
| 2014/0338753 A1 | 11/2014 | Sperling et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0017648 A1 | 1/2015 | Hiddessen et al. |
| 2015/0031034 A1 | 1/2015 | Hindson et al. |
| 2015/0034163 A1 | 2/2015 | Abate et al. |
| 2015/0050688 A1 | 2/2015 | Thrasher et al. |
| 2015/0066385 A1 | 3/2015 | Schnall-Levin et al. |
| 2015/0073061 A1 | 3/2015 | Bauer et al. |
| 2015/0224466 A1 | 8/2015 | Hindson et al. |
| 2015/0258543 A1 | 9/2015 | Baroud et al. |
| 2015/0267246 A1 | 9/2015 | Baroud et al. |
| 2015/0292988 A1* | 10/2015 | Bharadwaj ........ B01L 3/502784 506/40 |
| 2015/0298091 A1 | 10/2015 | Weitz et al. |
| 2015/0336096 A1 | 11/2015 | Smith et al. |
| 2015/0352597 A1 | 12/2015 | Deshpande et al. |
| 2015/0355071 A1 | 12/2015 | Gluckstad |
| 2015/0360236 A1 | 12/2015 | Garcia et al. |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0003729 A1 | 1/2016 | Lo et al. |
| 2016/0024558 A1 | 1/2016 | Hardenbol et al. |
| 2016/0053303 A1 | 2/2016 | Brenner et al. |
| 2016/0059204 A1 | 3/2016 | Hindson et al. |
| 2016/0091145 A1 | 3/2016 | Weitz et al. |
| 2016/0097087 A1 | 4/2016 | Wiyatno et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0250637 A1 | 9/2016 | Neild et al. |
| 2016/0257984 A1 | 9/2016 | Hardenbol et al. |
| 2016/0271576 A1 | 9/2016 | Arab et al. |
| 2016/0281136 A1 | 9/2016 | Jarosz et al. |
| 2016/0281137 A1 | 9/2016 | Jarosz et al. |
| 2016/0281138 A1 | 9/2016 | Jarosz et al. |
| 2016/0281160 A1 | 9/2016 | Jarosz et al. |
| 2016/0281161 A1 | 9/2016 | Jarosz et al. |
| 2016/0299053 A1 | 10/2016 | Jiang |
| 2016/0304860 A1 | 10/2016 | Hindson et al. |
| 2016/0314242 A1 | 10/2016 | Schnall-Levin et al. |
| 2016/0332163 A1 | 11/2016 | Wang et al. |
| 2016/0348093 A1 | 12/2016 | Price et al. |
| 2016/0362724 A1 | 12/2016 | Bailey et al. |
| 2017/0009274 A1 | 1/2017 | Abate et al. |
| 2017/0014824 A1 | 1/2017 | Boyd et al. |
| 2017/0016041 A1 | 1/2017 | Greenfield et al. |
| 2017/0028365 A1 | 2/2017 | Link et al. |
| 2017/0056884 A1 | 3/2017 | Hiddessen et al. |
| 2017/0065979 A1 | 3/2017 | Ness et al. |
| 2017/0080425 A1 | 3/2017 | Toner et al. |
| 2017/0106134 A1 | 4/2017 | Dreschel et al. |
| 2017/0114385 A1 | 4/2017 | Di Carlo et al. |
| 2017/0122861 A1 | 5/2017 | Lin |
| 2017/0128937 A1 | 5/2017 | Hung et al. |
| 2017/0128938 A9 | 5/2017 | Gilbert et al. |
| 2017/0128940 A1 | 5/2017 | Amini et al. |
| 2017/0128943 A1 | 5/2017 | Fraden et al. |
| 2017/0136461 A1 | 5/2017 | Smith et al. |
| 2017/0144161 A1 | 5/2017 | Hindson et al. |
| 2017/0145476 A1 | 5/2017 | Ryvkin et al. |
| 2017/0151536 A1 | 6/2017 | Weitz et al. |
| 2017/0159109 A1 | 6/2017 | Zheng et al. |
| 2017/0165663 A1 | 6/2017 | Hong et al. |
| 2017/0165669 A1 | 6/2017 | Hung et al. |
| 2017/0175179 A1 | 6/2017 | Hiddessen et al. |
| 2017/0235876 A1 | 8/2017 | Jaffe et al. |
| 2017/0246638 A1 | 8/2017 | Possinger et al. |
| 2017/0260584 A1 | 9/2017 | Zheng et al. |
| 2017/0282145 A1 | 10/2017 | Merten et al. |
| 2017/0291174 A1 | 10/2017 | Makarewicz, Jr. et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0056294 A1 | 3/2018 | Di Carlo et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0094313 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0142292 A1 | 5/2018 | Hindson et al. |
| 2018/0236443 A1 | 8/2018 | Masquelier et al. |
| 2018/0334670 A1 | 11/2018 | Bharadwaj et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0060906 A1 | 2/2019 | Bharadwaj et al. |
| 2019/0064173 A1 | 2/2019 | Bharadwaj et al. |
| 2019/0134633 A1 | 5/2019 | Bharadwaj et al. |
| 2019/0351417 A1 | 11/2019 | Bharadwaj et al. |
| 2020/0114358 A1 | 4/2020 | Bharadwaj et al. |
| 2020/0115703 A1 | 4/2020 | Bharadwaj et al. |
| 2020/0206742 A1 | 7/2020 | Bharadwaj et al. |
| 2020/0230606 A1 | 7/2020 | Bharadwaj et al. |
| 2020/0290048 A1 | 9/2020 | Bharadwaj et al. |

FOREIGN PATENT DOCUMENTS

| | | |
|---|---|---|
| WO | WO-2004/002627 A2 | 1/2004 |
| WO | WO-2004/091763 A2 | 10/2004 |
| WO | WO-2006/040551 A2 | 4/2006 |
| WO | WO-2007/140015 A2 | 12/2007 |
| WO | WO-2008/121342 A2 | 10/2008 |
| WO | WO-2010/104604 A1 | 9/2010 |
| WO | WO-2010/128858 A1 | 11/2010 |
| WO | WO-2012/013316 A1 | 2/2012 |
| WO | WO-2012/142664 A1 | 10/2012 |
| WO | WO-2012/156744 A2 | 11/2012 |
| WO | WO-2012/167142 A2 | 12/2012 |
| WO | WO-2013/096643 A1 | 6/2013 |
| WO | WO-2013/112121 A1 | 8/2013 |
| WO | WO-2014/028378 A2 | 2/2014 |
| WO | WO-2014/117784 A1 | 8/2014 |
| WO | WO-2014/165559 A2 | 10/2014 |
| WO | WO-2014/210353 A2 | 12/2014 |

(56) References Cited

FOREIGN PATENT DOCUMENTS

| WO | WO-2015/015199 A2 | 2/2015 |
|---|---|---|
| WO | WO-2015/076251 A1 | 5/2015 |
| WO | WO-2015/132317 A1 | 9/2015 |
| WO | WO-2015/132318 A1 | 9/2015 |
| WO | WO-2015/134984 A1 | 9/2015 |
| WO | WO-2015/157567 A1 | 10/2015 |
| WO | WO-2015/160919 A1 | 10/2015 |
| WO | WO-2015/164212 A1 | 10/2015 |
| WO | WO-2015/191534 A2 | 12/2015 |
| WO | WO-2015/200869 A1 | 12/2015 |
| WO | WO-2015/200871 A1 | 12/2015 |
| WO | WO-2015/200893 A2 | 12/2015 |
| WO | WO-2016/035284 A1 | 3/2016 |
| WO | WO-2016/065056 A1 | 4/2016 |
| WO | WO-2016/069939 A1 | 5/2016 |
| WO | WO-2016/075172 A1 | 5/2016 |
| WO | WO-2016/085742 A1 | 6/2016 |
| WO | WO-2016/087068 A1 | 6/2016 |
| WO | WO-2016/114970 A1 | 7/2016 |
| WO | WO-2016/115273 A1 | 7/2016 |
| WO | WO-2016/130578 A1 | 8/2016 |
| WO | WO-2016/137973 A1 | 9/2016 |
| WO | WO-2016/138148 A1 | 9/2016 |
| WO | WO-2016/149096 A1 | 9/2016 |
| WO | WO-2016/151107 A1 | 9/2016 |
| WO | WO-2016/168584 A1 | 10/2016 |
| WO | WO-2016/174229 A1 | 11/2016 |
| WO | WO-2016/187179 A1 | 11/2016 |
| WO | WO-2016/187256 A2 | 11/2016 |
| WO | WO-2016/193758 A1 | 12/2016 |
| WO | WO-2017/005872 A1 | 1/2017 |
| WO | WO-2017/015123 A1 | 1/2017 |
| WO | WO-2017/060876 A1 | 4/2017 |
| WO | WO-2017/070056 A1 | 4/2017 |
| WO | WO-2017/075549 A1 | 5/2017 |
| WO | WO-2017/083375 A1 | 5/2017 |
| WO | WO-2017/087910 A1 | 5/2017 |
| WO | WO-2017/096158 A1 | 6/2017 |
| WO | WO-2017/117490 A1 | 7/2017 |
| WO | WO-2017/138984 A1 | 8/2017 |
| WO | WO-2017/139690 A1 | 8/2017 |
| WO | WO-2017/180949 A1 | 10/2017 |
| WO | WO-2017/184707 A1 | 10/2017 |
| WO | WO-2017/197338 A1 | 11/2017 |
| WO | WO-2017/197343 A2 | 11/2017 |
| WO | WO-2018/039338 A1 | 3/2018 |
| WO | WO-2018/075693 A1 | 4/2018 |
| WO | WO-2018/213643 A1 | 11/2018 |
| WO | WO-2018/226546 A1 | 12/2018 |
| WO | WO-2019/040637 A1 | 2/2019 |
| WO | WO-2020/139844 A1 | 7/2020 |

OTHER PUBLICATIONS

Aghvami et al., "Rapid prototyping of cyclic olefin copolymer (COC) microfluidic devices," Sens Actuators B Chem. 247: 940-949 (2017).
Akartuna et al., "Chemically induced coalescence in droplet-based microfluidics," Lab Chip. DOI:10.1039/c4lc01285b (2014) (5 pages).
Akselband et al., "Enrichment of slow-growing marine microorganisms from mixed cultures using gel microdrop (GMD) growth assay and fluorescence-activated cell sorting," J Exp Mar Bio Ecol. 329(2): 196-205 (2006).
Akselband et al., "Rapid mycobacteria drug susceptibility testing using Gel Microdrop (GMD) Growth Assay and flow cytometry," J Microbiol Methods. 62(2): 181-197 (2005).
Anna et al., "Formation of dispersions using 'flow focusing' in microchannels," Appl Phys Lett. 82(3): 364-366 (2003).
Attia et al., "Micro-injection moulding of polymer microfluidic devices," Microfluid Nanofluidics. 7(1): 1-28 (2009) (30 pages).
Baret et al., "Fluorescence-activated droplet sorting (FADS): efficient microfluidic cell sorting based on enzymatic activity," Lab Chip. 9(13): 1850-1859 (2009).
Baret, "Surfactants in droplet-based microfluidics," Lab Chip. 12(3): 422-433 (2012).
Becker et al., "Polymer microfabrication technologies for microfluidic systems," Anal Bioanal Chem. 390(1): 89-111 (2008).
Beer et al., "On-chip, real-time, single-copy polymerase chain reaction in picoliter droplets," Anal Chem. 79(22): 8471-8475 (2007).
Boone et al. "Plastic advances microfluidic devices," Anal Chem. 74(3): 78A-86A (2002).
Braeckmans et al., "Scanning the code. Encoded microcarrier beads signal the way to better combinatorial libraries and biological assays," Modern Drug Discovery. 6(2):28-30; 32 (2003) (4 pages).
Bransky et al., "A microfluidic droplet generator based on a piezoelectric actuator," Lab Chip. 9(4): 516-520 (2009).
Brouzes et al., "Droplet microfluidic technology for single-cell high-throughput screening," Proc Natl Acad Sci U S A. 106(34): 14195-14200 (2009).
Burns et al., "An integrated nanoliter DNA analysis device," Science. 282(5388): 484-487 (1998).
Burns et al., "Microfabricated structures for integrated DNA analysis," Proc Natl Acad Sci U S A. 93(11): 5556-5561 (1996).
Burns et al., "The intensification of rapid reactions in multiphase systems using slug flow in capillaries," Lab Chip. 1(1): 10-15 (2001).
Carroll et al. "The selection of high-producing cell lines using flow cytometry and cell sorting," Expert Opin Biol Ther. 4(11): 1821-1829 (2004).
Chakraborty et al., "Microfluidic step-emulsification in axisymmetric geometry," Lab Chip. 17(21): 3609-3620 (2017).
Chechetkin et al. "Sequencing by hybridization with the generic 6-mer oligonucleotide microarray: an advanced scheme for data processing," J Biomol Struct Dyn. 18(1): 83-101 (2000).
Chen et al. "Chemical transfection of cells in picoliter aqueous droplets in fluorocarbon oil," Anal Chem. 83(22): 8816-8820 (2011).
Chien et al., "Multiport flow-control system for lab-on-a-chip microfluidic devices," Fresenius J Anal Chem. 371(2): 106-11 (2001).
Chokkalingam et al., "Probing cellular heterogeneity in cytokine-secreting immune cells using droplet-based microfluidics," Lab Chip. 13(24): 4740-4744 (2013).
Chokkalingam et al., "Self-synchronizing pairwise production of monodisperse droplets by microfluidic step emulsification," Appl Phys Lett. 93(25): 254101-1-254101-3 (2008).
Chou et al., "Disposable microdevices for DNA analysis and cell sorting," Proc Solid-State Sensor and Actuator Workshop, Jun. 8-11, Hilton Head, SC, pp. 11-14 (1998).
Chu et al., "Controllable monodisperse multiple emulsions," Angew Chem Int Ed. 46(47): 8970-8974 (2007).
Clausell-Tormos et al., "Droplet-based microfluidic platforms for the encapsulation and screening of mammalian cells and multicellular organisms," Chem Biol. 15(5):427-437 (2008).
Curcio, Mario, Thesis: "Improved techniques for high-throughput molecular diagnostics," Doctor of Philosophy, Royal Institute of Technology, 2002 (131 pages).
Damean et al., "Simultaneous measurement of reactions in microdroplets filled by concentration gradients," Lab Chip. 9(12): 1707-1713 (2009).
Dangla et al., "Droplet microfluidics driven by gradients of confinement," Proc Natl Acad Sci U S A. 110(3): 853-858 (2013).
Dangla et al., "The physical mechanisms of step emulsification," J Phys D Appl Phys. 46(11):114003 (2013) (8 pages).
De Bruin et al., "UBS investment research: Q-Series: DNA sequencing," UBS Securities LLC. Jul. 12, pp. 1-15 (2007).
De Mello et al., Chip technology for micro-separation. *Microsystem Technology: Biomethods*, vol. 10. Köhler J.M., Mejevaia T., Saluz H.P., 129-177 (1999).
Demirci et al., "Single cell epitaxy by acoustic picolitre droplets," Lab Chip. 7(9): 1139-1145 (2007).
Doerr, "The smallest bioreactor," Nat Methods. 2(5): 326 (2005).
Dowding et al., "Oil core/polymer shell microcapsules by internal phase separation from emulsion droplets. II: Controlling the release profile of active molecules," Langmuir. 21(12): 5278-5284 (2005).

(56) References Cited

OTHER PUBLICATIONS

Draper et al., "Compartmentalization of electrophoretically separated analytes in a multiphase microfluidic platform," Anal Chem. 84(13): 5801-5808 (2012).
Dressler et al., "Droplet-based microfluidics: enabling impact on drug discovery," J Biomol Screen. 19(4): 483-496 (2014).
Drmanac et al., "Sequencing by hybridization (SBH): advantages, achievements, and opportunities," Adv Biochem Eng Biotechnol. 77: 75-101 (2002).
Duffy et al., "Rapid prototyping of microfluidic systems in poly(dimethylsiloxane)," Anal Chem. 70(23): 4974-4984 (1998).
Eastburn et al., "Ultrahigh-throughput mammalian single-cell reverse-transcriptase polymerase chain reaction in microfluidic drops," Anal Chem. 85(16): 8016-8021 (2013).
Eggersdorfer et al., "Supplementary Information: Tandem emulsification for high-throughput production of double emulsions," Lab Chip. 17(5):936-942 (2017) (2 pages).
Eggersdorfer et al., "Tandem emulsification for high-throughput production of double emulsions," Lab Chip. 17(5): 936-942 (2017).
Esser-Kahn et al., "Triggered release from polymer capsules," Macromolecules. 44(14): 5539-5553 (2011).
Fisher et al., "A scalable, fully automated process for construction of sequence-ready human exome targeted capture libraries," Genome Biol. 12(1):R1 (2011) (15 pages).
Fredrickson et al., "Macro-to-micro interfaces for microfluidic devices," Lab Chip. 4(6): 526-533 (2004).
Freiberg et al., "Polymer microspheres for controlled drug release," Int J Pharm. 282(1-2): 1-18 (2004).
Fu et al., "A microfabricated fluorescence-activated cell sorter," Nature Biotechnol. 17(11): 1109-1111 (1999).
Fulton et al., "Advanced multiplexed analysis with the FlowMetrix system," Clin Chem. 43(9): 1749-1756 (1997).
Gai et al., "Spatiotemporal periodicity of dislocation dynamics in a two-dimensional microfluidic crystal flowing in a tapered channel," Proc Natl Acad Sci U S A. 113(43):12082-12087 (2016).
Gai et al., "Supporting Information: Spatiotemporal periodicity of dislocation dynamics in a two-dimensional microfluidic crystal flowing in a tapered channel," Proc Natl Acad Sci U S A. 1-9 (2016).
Galambos et al., "Precision alignment packaging for microsystems with multiple fluid connections," Proceedings of 2001 ASME: International Mechanical Engineering Conference and Exposition, Nov. 11-16, New York, NY. pp. 1-8 (2001).
Garstecki et al., "Formation of monodisperse bubbles in a microfluidic flow-focusing device," Appl Phys Lett. 85(13): 2649-2651 (2004).
Gartner et al., "The microfluidic toolbox—examples for fluidic interfaces and standardization concepts," Proc SPIE Int Soc Opt Eng. (2003) (6 pages).
Ghadessy et al., "Directed evolution of polymerase function by compartmentalized self replication," Proc Natl Acad Sci U S A. 98(8): 4552-4557 (2001).
Granieri, Lucia, Thesis: "Droplet-based microfluidics and engineering of tissue plasminogen activator for biomedical applications," Doctor of Philosophy, L'Universite de Strasbourg, 2009 (131 pages).
Grasland-Mongrain et al., "Droplet coalescence in microfluidic devices," <http://www.eleves.ens.fr./home/grasland/rapports/stage4.pdf>, retrieved Jun. 4, 2007 (2003) (31 pages).
Guo et al., "Droplet microfluidics for high-throughput biological assays," Lab Chip. 21(12): 2146-2155 (2012).
Gyarmati et al., "Reversible disulphide formation in polymer networks: A versatile functional group from synthesis to applications," Eur Polym J. 49(6): 1268-1286 (2013).
Hashimshony et al., "CEL-Seq: Single-cell RNA-seq by multiplexed linear amplification," Cell Rep. 2(3): 666-673 (2012) (14 pages).
Hati et al., "Production of monodisperse drops from viscous fluids," Lab Chip. DOI: 10.1039/c7lc01322a (2018) (7 pages).
He et al., "Selective encapsulation of single cells and subcellular organelles into picoliter- and femtoliter-volume droplets," Anal Chem. 77(6): 1539-1544 (2005).

Holtze et al., "Biocompatible surfactants for water-in-fluorocarbon emulsions," Lab Chip. 8(10): 1632-1639 (2008).
Hosokawa et al., "Massively parallel whole genome amplification for single-cell sequencing using droplet microfluidics," Sci Rep. 7(1): 5199 (2017) (11 pages).
Huang et al., "Coating of poly(dimethylsiloxane) with n-dodecyl-Beta-D-maltoside to minimize nonspecific protein adsorption," Lab Chip. 5(10):1005-1007 (2005).
Huang et al., "Collective generation of milliemulsions by step-emulsification," RSC Adv. 7(24): 14932-14938 (2017).
Huebner et al., "Quantitative detection of protein expression in single cells using droplet microfluidics," Chem Commun. 12:1218-1220 (2007).
Hug et al., "Measurement of the number of molecules of a single mRNA species in a complex mRNA preparation," J Theor Biol. 221(4): 615-624 (2003).
Hwang et al., "Surface modification of cyclic olefin copolymer substrate by oxygen plasma treatment," Surf Coat Tech. 202(15): 3669-3674 (2008).
Jung et al., "Micro machining of injection mold inserts for fluidic channel of polymeric biochips," Sensors. 7(8): 1643-1654 (2007).
Kahkeshani et al., "Drop formation using ferrofluids driven magnetically in a step emulsification device," Lab Chip. 16(13): 2474-2480 (2016).
Jena et al., "Cyclic olefin copolymer based microfluidic devices for biochip applications: Ultraviolet surface grafting using 2-methacryloyloxyethyl phosphorylcholine," Biomicrofluidics. 6(1): 012822-1-012822-12 (2012) (12 pages).
Katsura et al., "Indirect micromanipulation of single molecules in water-in-oil emulsion," Electrophoresis. 22(2): 289-293 (2001).
Kawai et al., Mass-production system of nearly monodisperse diameter gel particles using droplets formation in a microchannel. *Micro Total Analysis Systems 2002*, vol. 1. Baba Y., Shoji S., van den Berg A., 368-370 (2002).
Kenis et al., "Microfabrication inside capillaries using multiphase laminar flow patterning," Science. 285(5424): 83-85 (1999).
Khomiakova et al., "Analysis of perfect and mismatched DNA duplexes by a generic hexanucleotide microchip," Mol Biol (Mosk). 37(4): 726-741 (2003) (English abstract only) (1 page).
Kim et al., "Albumin loaded microsphere of amphiphilic poly(ethylene glycol)/poly(alpha-ester) multiblock copolymer," Eur J Pharm Sci. 23(3): 245-251 (2004).
Kim et al., "Fabrication of monodisperse gel shells and functional microgels in microfluidic devices," Angew Chem Int Ed Engl. 46(11): 1819-1822 (2007) (5 pages).
Kim et al., "Rapid prototyping of microfluidic systems using a PDMS/polymer tape composite," Lab Chip. 9(9): 1290-1293 (2009).
Klein et al., "Droplet barcoding for single-cell transcriptomics applied to embryonic stem cells," Cell. 161(5): 1187-1201 (2015) (22 pages).
Kobayashi et al., "Effect of slot aspect ratio on droplet formation from silicon straight-through microchannels," J Colloid Interface Sci. 279(1): 277-80 (2004).
Kobayashi et al., "Preparation characteristics of oil-in-water emulsions using differently charged surfactants in straight-through microchannel emulsification," Colloids Surf A Physicochem Eng Asp. 229(1-3): 33-41 (2003).
Köster et al., "Drop-based microfluidic devices for encapsulation of single cells," Lab Chip. 8(7): 1110-1115 (2008).
Lagally et al., "Single-molecule DNA amplification and analysis in an integrated microfluidic device," Anal Chem. 73(3): 565-570 (2001).
Lagus et al., "A review of the theory, methods, and recent applications of high-throughput single-cell droplet microfluidics," J Phys D: Appl Phys. 46: 114005 (21 pages) (2013).
Li et al., "Step-emulsification in a microfluidic device," Lab Chip. 15(4): 1023-31 (2015) (10 pages).
Li et al., Microfluidic Lab-on-a-Chip. *Ewing's Analytical Instrumentation Handbook* . . . Cazes, J., 581-679 (2005) (120 pages).
Loscertales et al., "Micro/nano encapsulation via electrified coaxial liquid jets," Science. 295(5560): 1695-1698 (2002).

(56) References Cited

OTHER PUBLICATIONS

Love et al., "A microengraving method for rapid selection of single cells producing antigen specific antibodies," Nat Biotechnol. 24(6): 703-707 (2006).
Lowe, Adam, Thesis: "Norbornenes and [n]polynorbornanes as molecular scaffolds for anion recognition," Doctor of Philosophy, Deakin University, 2010 (361 pages).
Maan et al., "Microfluidic emulsification in food processing," J Food Eng. 147:1-7 (2015).
Maan et al., "Spontaneous droplet formation techniques for monodisperse emulsions preparation—Perspectives for food applications," J Food Eng. 107(3-4):334-46 (2011).
Macosko et al., "Supplemental Information: Highly parallel genome-wide expression profiling of individual cells using nanoliter droplets," Cell. 161(5): 1202-1214 (2015) (31 pages).
Mair et al., "Injection molded microfluidic chips featuring integrated interconnects," Lab Chip. 6(10): 1346-1354 (2006).
Makino et al., "Preparation of hydrogel microcapsules effects of preparation conditions upon membrane properties," Colloids Surf B Biointerfaces. 12(2): 97-104 (1998).
Man, Piu, Dissertation: "Monolithic structures for integrated microfluidic analysis," Doctor of Philosophy, The University of Michigan, 2001 (144 pages).
Mazutis et al., "Selective droplet coalescence using microfluidic systems," Lab Chip. 12(10): 1800-1806 (2012).
Mazutis et al., "Single-cell analysis and sorting using droplet-based microfluidics," available in PMC Aug. 11, 2014. Published in final edited form as Nat Protoc. 8(5): 870-891 (2013) (48 pages).
Merriman et al., "Progress in ion torrent semiconductor chip based sequencing," Electrophoresis. 33(23): 3397-3417 (2012).
Mittal et al., "Dynamics of step-emulsification: From a single to a collection of emulsion droplet generators," Phys Fluids. 26: 082109-1-082109-14 (2014).
Moore et al., "Behavior of capillary valves in centrifugal microfluidic devices prepared by three-dimensional printing," Microfluid Nanofluid. 10(4): 877-888 (2011).
Navin, "The first five years of single-cell cancer genomics and beyond," Genome Res. 25(10): 1499-1507 (2015).
Nisisako et al., "Droplet formation in a microchannel network," Lab Chip. 2(1): 24-26 (2002).
Nisisako et al., "Droplet formation in a microchannel on PMMA plate," *Micro Total Analysis Systems 2001*. Ramsey, J.M., van den Berg, A., 137-138 (2001).
Nisisako et al., "Microfluidic large-scale integration on a chip for mass production of monodisperse droplets and particles," Lab Chip. 8(2):287-293 (2008).
Novak et al., "Single cell multiplex gene detection and sequencing using microfluidically-generated agarose emulsions," available in PMC Jan. 10, 2012, published in final edited form as: Angew Chem Int Ed Engl. 50(2):390-5 (2011) (10 pages).
Oberholzer et al., "Polymerase chain reaction in liposomes," Chem Biol. 2(10):677-82 (1995).
Ogawa et al., "Production and characterization of O/W emulsions containing cationic droplets stabilized by lecithin-chitosan membranes," J Agric Food Chem. 51(9):2806-12 (2003).
Okushima et al., "Controlled Production of Monodisperse Double Emulsions by Two-Step Droplet Breakup in Microfluidic Devices," Langmuir. 20(23):9905-8 (2004).
Perez et al., "Poly(lactic acid)-poly(ethylene glycol) nanoparticles as new carriers for the delivery of plasmid DNA," J Control Release. 75(1-2):211-24 (2001).
Pirie et al., "The Measurement of Wettability," J Chem Educ. 50(10):682-684 (1973).
Priest et al., "Generation of monodisperse gel emulsions in a microfluidic device," Appl Phys Lett. 88: 024106-1-024106-3 (2006).
Ramsey, "The burgeoning power of the shrinking laboratory" Nat Biotechnol. 17(11):1061-2 (1999).
Rotem et al., "High-throughput single-cell labeling (Hi-SCL) for RNA-Seq using drop-based microfluidics," PLoS One. 10(5):e0116328 (2015) (14 pages).
Rotem et al., "Single cell chip-seq using drop-based microfluidics," Frontiers of Single Cell Analysis, Sep. 5-7, Stanford, CA. Abstract 50 (2013) (1 page).
Ryan et al., "Rapid assay for mycobacterial growth and antibiotic susceptibility using gel microdrop encapsulation," J Clin Microbiol. 33(7):1720-6 (1995).
Sahin et al., "Microfluidic EDGE emulsification: the importance of interface interactions on droplet formation and pressure stability," Sci Rep. 6:26407 (2016) (7 pages).
Schirinzi et al., "Combinatorial sequencing-by-hybridization: Analysis of the NF1 gene," Genet Test. 10(1):8-17 (2006).
Schmitt et al., "Bead-based multiplex genotyping of human papillomaviruses," J Clin Microbiol. 44(2):504-12 (2006).
Schuler et al., "Digital droplet PCR on disk," Lab Chip. 16 (1): 208-216 (2016).
Seiffert et al., "Smart microgel capsules from macromolecular precursors," J Am Chem Soc. 132(18):6606-9 (2010).
Shah et al., "Fabrication of monodisperse thermosensitive microgels and gel capsules in microfluidic devices," Soft Matter. 4:2303-9 (2008).
Shim et al., "Supporting Information: Control and measurement of the phase behavior of aqueous solutions using microfluidics," S1-S13 (2007) (13 pages).
Song et al., "Reactions in droplets in microfluidic channels," Angew Chem Int Ed Engl. 45(44):7336-56 (2006).
Stolovicki et al., "Throughput enhancement of parallel step emulsifier devices by shear-free and efficient nozzle clearance," Lab Chip. DOI: 10.1039/c7lc01037k (2017) (7 pages).
Su et al., "Microfluidics-Based Biochips: Technology Issues, Implementation Platforms, and Design-Automation Challenges," IEEE Transactions on Computer-Aided Design of Integrated Circuits and Systems. 25(2):211-23 (2006).
Sun et al., "Progress in research and application of liquid phase chip technology," China Journal of Experimental Surgery. 22(5) (2005) (5 pages).
Tawfik et al. "Man-made cell-like compartments for molecular evolution," Nat Biotechnol. 16(7):652-6 (1998).
Tewhey et al., "Microdroplet-based PCR enrichment for large-scale targeted sequencing," Nat Biotechnol. 27(11):1025-31 (2009) (11 pages).
Theberge et al., "Microdroplets in microfluidics: an evolving platform for discoveries in chemistry and biology," Angew Chem Int Ed Engl. 49(34):5846-68 (2010).
Thorsen et al., "Dynamic pattern formation in a vesicle-generating microfluidic device," Phys Rev Lett. 86(18):4163-6 (2001).
Tubeleviciute et al., "Compartmentalized self-replication (CSR) selection of Thermococcus litoralis Sh1B DNA polymerase for diminished uracil binding," Protein Eng Des Sel. 23(8):589-97 (2010).
Turner et al., "Methods for genomic partitioning," Annu Rev Genomics Hum Genet. 10:263-84 (2009) (24 pages).
Van Dijke et al., "EDGE emulsification for food-grade dispersions," J Food Eng. 97(3): 348-354 (2010).
Van Dijke et al., "Effect of viscosities of dispersed and continuous phases in microchannel oil-in-water emulsification," Microfluid Nanofluid. 9(1):77-85 (2010).
Van Dijke et al., "Microchannel Emulsification: From Computational Fluid Dynamics to Predictive Analytical Model," Langmuir. 24(18): 10107-10115 (2008).
Van Dijke et al., "Parallelized edge-based droplet generation (EDGE) devices," Lab Chip. 9(19): 2824-2830 (2009).
Van Dijke et al., "Simultaneous Formation of Many Droplets in a Single Microfluidic Droplet Formation Unit," AlChE J. 56(3): 833-836 (2010).
Van Dijke et al., "The mechanism of droplet formation in microfluidic EDGE systems," Soft Matter. 6(2): 321-330 (2010).
Wagner et al., "Biocompatible fluorinated polyglycerols for droplet microfluidics as an alternative to PEG-based copolymer surfactants," Lab Chip. 16(1):65-9 (2016) (7 pages).
Wang et al., "A novel thermo-induced self-bursting microcapsule with magnetic-targeting property," Chemphyschem. 10(14):2405-9 (2009).

(56) References Cited

OTHER PUBLICATIONS

Ward et al., "Microfluidic flow focusing: drop size and scaling in pressure versus flow-rate-driven pumping," Electrophoresis. 26(19):3716-24 (2005).
Weaver et al., "Rapid clonal growth measurements at the single-cell level: gel microdroplets and flow cytometry," Biotechnology (N Y). 9(9):873-7 (1991).
Weigl et al., "Microfluidic diffusion-based separation and detection," Science. 283:346-7 (1999) (4 pages).
Whitesides et al., "Flexible methods for microfluidics," Phys Today. 54(6): 42-48 (2001).
Williams et al., "Amplification of complex gene libraries by emulsion PCR," Nat Methods. 3(7):545-50 (2006).
Zeng et al., "High-performance single cell genetic analysis using microfluidic emulsion generator arrays," Anal Chem. 82(8):3183-90 (2010).
Zhao et al., "Preparation of hemoglobin-loaded nano-sized particles with porous structure as oxygen carriers," Biomaterials. 28(7):1414-22 (2007).
Zilionis et al., "Single-cell barcoding and sequencing using droplet microfluidics," Nat Protoc. 12(1): 44-73 (2017).
Zong et al., "Genome-wide detection of single-nucleotide and copy-number variations of a single human cell," Science. 338(6114):1622-6 (2012) (6 pages).
International Search Report and Written Opinion for International Application No. PCT/US2018/056766, dated Feb. 1, 2019 (23 pages).
Cheung et al., "Characterization of acoustic droplet formation in a microfluidic flow-focusing device," Phys Rev E Stat Nonlin Soft Matter Phys. 84(6 Pt 2):066310. doi: 10.1103/PhysRevE.84.066310 (2011) (10 pages).

\* cited by examiner

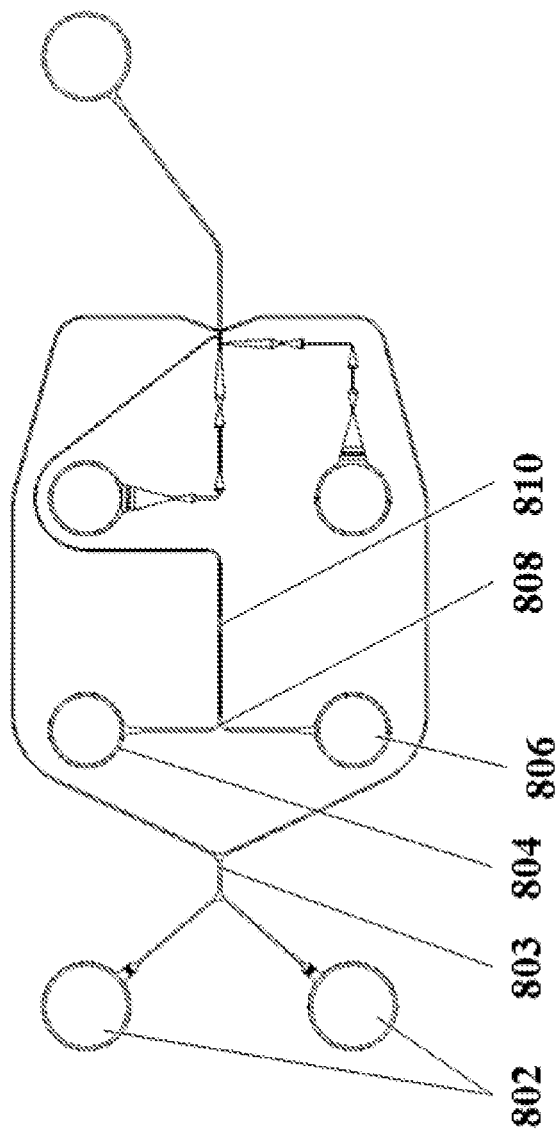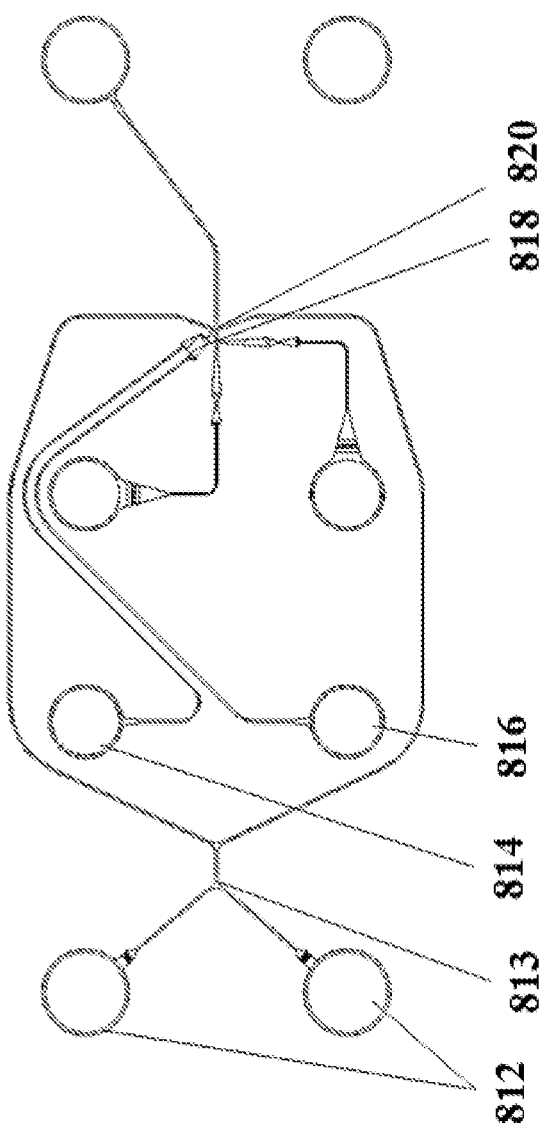

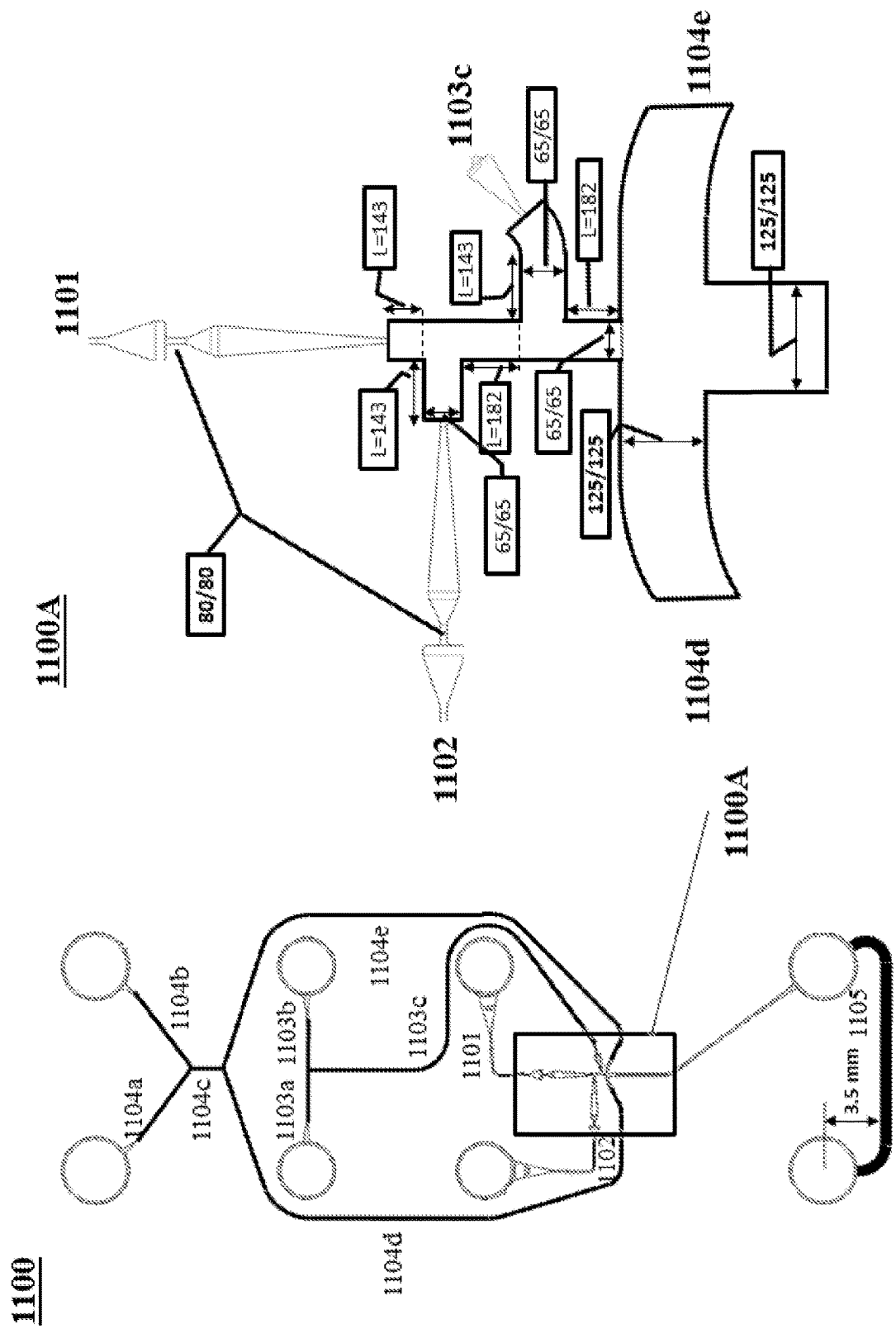

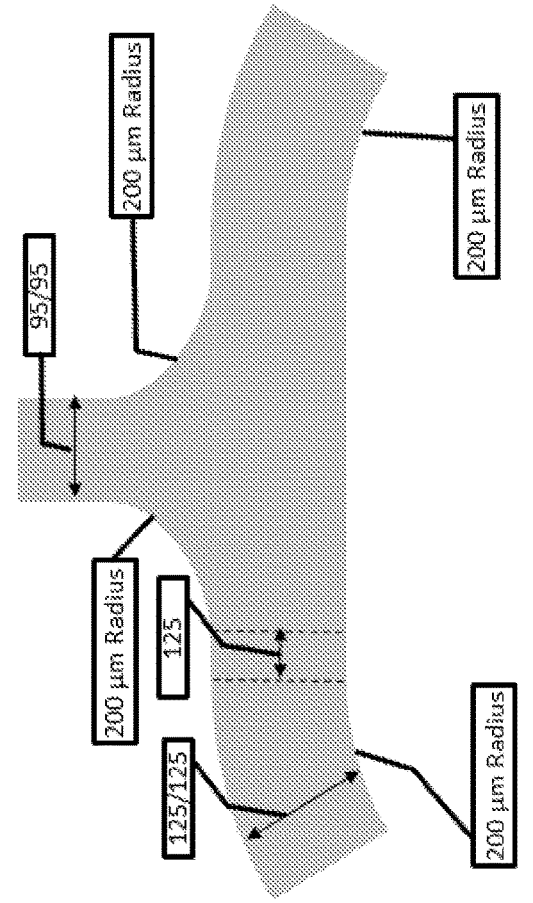
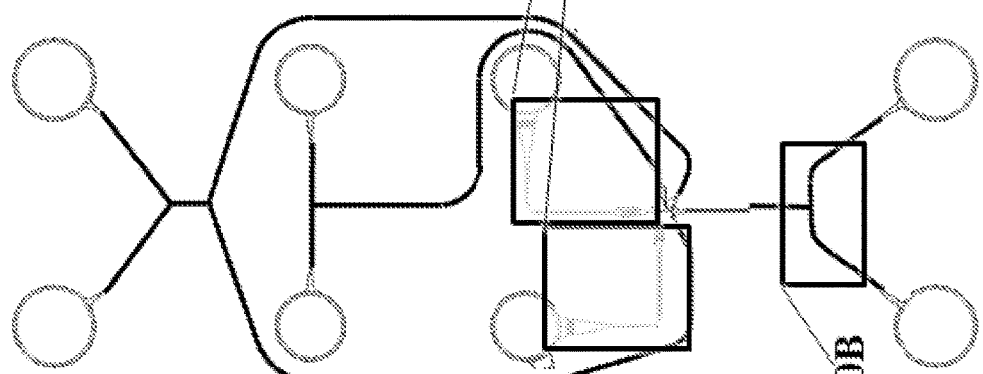
*FIG. 13A*
*FIG. 13B*

MICROFLUIDIC CHANNEL NETWORKS FOR PARTITIONING

CROSS-REFERENCE

This application claims the benefit of U.S. Provisional Patent Application No. 62/577,402, filed Oct. 26, 2017, which application is entirely incorporated by reference herein.

BACKGROUND

Samples may be processed for various purposes, such as identification of a type of moiety within the sample. The sample may be a biological sample. The biological samples may be processed for various purposes, such as detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

Recognized herein is a need for microfluidics systems, devices, and networks for generating partitions with high throughput and high consistency (e.g., monodispersity). The microfluidics systems, devices, and networks provided herein may have configurations that stabilize the fluid flow dynamics of the one or more fluids communicating in the channel networks, such as to generate partitions with high throughput and high consistency.

In an aspect, provided is a method for generating a plurality of droplets, comprising: (a) directing a first fluid along a first channel and a second fluid along a second channel to an intersection of at least the first channel and the second channel, to form a plurality of droplets upon the first fluid coming in contact with the second fluid; (b) collecting the plurality of droplets in an output reservoir; and (c) draining an excess of the second fluid from the output reservoir through a third channel to a drainage reservoir using at least a hydrostatic pressure differential between the output reservoir and the drainage reservoir.

In some embodiments, the excess of the second fluid from the output reservoir is drained through a plurality of drainage channels including the third channel to the drainage reservoir.

In some embodiments, the excess of the second fluid from the output reservoir is drained through a plurality of drainage channels including the third channel to a plurality of drainage reservoirs including the drainage reservoir.

In some embodiments, the method further comprises directing a third fluid along a fourth channel to contact the first fluid at or before the intersection, wherein the third fluid is immiscible with the second fluid.

In some embodiments, the plurality of droplets has a higher density than the second fluid. In some embodiments, the third channel is located above a predetermined threshold level in the output reservoir.

In some embodiments, the plurality of droplets has a lower density than the second fluid. In some embodiments, the third channel is located below a predetermined threshold level in the output reservoir.

In some embodiments, the first fluid is immiscible with the second fluid.

In some embodiments, the first fluid comprises one or more reagents.

In some embodiments, the first fluid comprises a plurality of particles. In some embodiments, the plurality of particles comprises a plurality of biological particles. In some embodiments, the plurality of biological particles includes cells or derivatives thereof. In some embodiments, the plurality of particles comprises a plurality of particles having coupled thereto a plurality of barcodes. In some embodiments, a given droplet of the plurality of droplets includes a given biological particle from a plurality of biological particles and/or a given particle having coupled thereto a given barcode of a plurality of barcodes. In some embodiments, the method further comprises, subsequent to (b), subjecting nucleic acid molecules derived from the given biological particle to nucleic acid sequencing. In some embodiments, the method further comprises, subsequent to (b), subjecting the given droplet to nucleic acid amplification conditions to yield amplification products of the nucleic acid molecules derived from the given biological particle. In some embodiments, the method further comprises subjecting the amplification products to nucleic acid sequencing.

In another aspect, provided is a method for generating a plurality of droplets, comprising: (a) directing a first fluid along a first channel and a second fluid along a second channel to a intersection of the first channel and the second channel, and directing the first fluid and the second fluid along a third channel from the intersection to come in contact with a third fluid, wherein respective lengths of the first channel and the second channel are greater than a length of the third channel; (b) generating the plurality of droplets upon the first fluid and the second fluid coming in contact with the third fluid, wherein the third fluid is immiscible with the first fluid and the second fluid; and (c) collecting the plurality of droplets in an output reservoir In some embodiments, the respective lengths of the first channel and the second channel are substantially equal.

In some embodiments, a difference between the respective lengths of the first channel and the second channel is less than 1 millimeter.

In some embodiments, the first channel or the second channel or both has one or more fluid pinning features at or upstream of the intersection.

In some embodiments, the first channel or the second channel or both has one or more frictional elements at or upstream of the intersection to decrease or disrupt fluid flow of the first fluid or the second fluid or both at or upstream of the intersection, respectively. In some embodiments, the one or more frictional elements comprise decreased cross-sectional area of a channel, textures or patterns disposed on an inner wall of the channel, a protrusion in the channel, or a coating on the inner wall of the channel.

In some embodiments, the third fluid comes in contact with the first fluid and the second fluid in the output reservoir. In some embodiments, the third fluid is substantially stationary in the output reservoir.

In some embodiments, the first fluid and the second fluid are the same type of fluid. In some embodiments, the same type of fluid comprises one or more reagents. In some embodiments, the same type of fluid has a contact angle of greater than about 60° and less than about 90°.

In some embodiments, the method further comprises, prior to (b), directing the third fluid along a fourth channel to come in contact with the first fluid and the second fluid.

In some embodiments, (b) comprises the third fluid coming in contact with a fourth fluid, wherein the fourth fluid comprises the first fluid and the second fluid and a plurality of particles. In some embodiments, the plurality of particles comprises a plurality of biological particles. In some embodiments, the plurality of biological particles includes cells or derivatives thereof. In some embodiments, the plurality of particles comprises a plurality of particles having coupled thereto a plurality of barcodes. In some embodiments, a given droplet of the plurality of droplets includes a given biological particle from a plurality of biological particles and/or a given particle having coupled thereto a given barcode of a plurality of barcodes. In some embodiments, the method further comprises, subsequent to (c), subjecting nucleic acid molecules derived from the given biological particle to nucleic acid sequencing. In some embodiments, the method further comprises, subsequent to (c), subjecting the given droplet to nucleic acid amplification conditions to yield amplification products of the nucleic acid molecules derived from the given biological particle. In some embodiments, the method further comprises subjecting the amplification products to nucleic acid sequencing.

In another aspect, provided is a system for generating a plurality of droplets, comprising: a fluid flow path comprising a first channel, a second channel, a third channel, a fourth channel fluidically connecting an output reservoir and a drainage reservoir, and an intersection of the first channel and the second channel; at least one fluid flow unit that is configured to (i) subject a first fluid to flow along the first channel and a second fluid to flow along the second channel to the intersection, and (ii) subject a plurality of droplets to flow along the third channel to the output reservoir; and a controller operatively coupled to the fluid flow unit, wherein the controller is configured to direct the at least one fluid flow unit to (i) subject the first fluid to flow along the first channel towards the intersection and (ii) the second fluid to flow along the second channel towards the intersection, to generate the plurality of droplets upon the first fluid coming in contact with the second fluid, which plurality of droplets is subjected to flow along the third channel to the output reservoir, wherein the fourth channel is configured to permit an excess of the second fluid to be drained from the output reservoir to the drainage reservoir using at least a hydrostatic pressure differential between the output reservoir and the drainage reservoir.

In some embodiments, the first fluid comprises a plurality of particles. In some embodiments, during use, the plurality of particles comprises a plurality of biological particles and/or a plurality of particles having coupled thereto a plurality of barcodes.

In some embodiments, the at least one fluid flow unit includes at least one pump that is configured to provide negative pressure. In some embodiments, the at least one fluid flow unit includes at least one compressor that is configured to provide positive pressure. In some embodiments, the at least one fluid flow unit includes an actuator.

In some embodiments, the system further comprises a plurality of drainage reservoirs, including the drainage reservoir, fluidically connected to the output reservoir via a plurality of drainage channels, including the fourth channel.

In some embodiments, the plurality of droplets has a higher density than the second fluid. In some embodiments, the fourth channel is located above a predetermined threshold level in the output reservoir.

In some embodiments, the plurality of droplets has a lower density than the second fluid. In some embodiments, the fourth channel is located below a predetermined threshold level in the output reservoir.

In another aspect, provided is a system for generating a plurality of droplets, comprising: a fluid flow path comprising a first channel, a second channel, a third channel, and an intersection of the first channel, the second channel, and the third channel, wherein respective lengths of the first channel and the second channel are greater than a length of the third channel; at least one fluid flow unit that is configured to (i) subject a first fluid to flow along the first channel and a second fluid to flow along the second channel to the intersection, and (ii) subject the first fluid and the second fluid to flow along the third channel from the intersection; and a controller operatively coupled to the fluid flow unit, wherein the controller is programmed to direct the at least fluid flow unit to (i) subject the first fluid to flow along the first channel towards the intersection and subject the second fluid to flow along the second channel towards the intersection, and (ii) subject the first fluid and the second fluid to flow along the third channel from the intersection towards a third fluid, to generate the plurality of droplets upon the first fluid and the second fluid coming in contact with the third fluid, wherein the third fluid is immiscible with the first fluid and the second fluid.

In some embodiments, the first fluid or the second fluid comprises a plurality of particles. In some embodiments, the plurality of particles comprises a plurality of biological particles and/or a plurality of particles having coupled thereto a plurality of barcodes.

In some embodiments, the at least one fluid flow unit includes at least one pump that is configured to provide negative pressure. In some embodiments, the at least one fluid flow unit includes at least one compressor that is configured to provide positive pressure. In some embodiments, the at least one fluid flow unit includes an actuator.

In some embodiments, the system further comprises a fourth channel, wherein the at least one fluid flow unit is configured to subject the third fluid to flow along the fourth channel to come into contact with the first fluid and the second fluid.

In some embodiments, the system further comprises an output reservoir fluidically connected to the intersection by the third channel, wherein the third fluid is substantially stationary in the output reservoir.

In some embodiments, the first channel or the second channel or both has one or more fluid pinning features at or upstream of the intersection.

In some embodiments, the first channel or the second channel or both has one or more frictional elements at or upstream of the intersection to decrease or disrupt fluid flow of the first fluid or the second fluid or both at or upstream of the intersection, respectively. In some embodiments, the one or more frictional elements comprise decreased cross-sectional area of a channel, textures or patterns disposed on an inner wall of the channel, a protrusion in the channel, or a coating on the inner wall of the channel.

In another aspect, provided is a method for generating a plurality of droplets, comprising: (a) directing a first fluid from a first input source along a first channel and a second fluid from a second input source along a second channel to an intersection of the first channel and the second channel; (b) directing a third fluid along a third channel to the intersection or a location downstream of the intersection, wherein the third fluid is immiscible with the first fluid and the second fluid; (c) generating the plurality of droplets upon the first fluid and the second fluid coming in contact with the third fluid; (d) directing the plurality of droplets along a fourth channel to an output reservoir; and (e) draining an excess of the third fluid from the output reservoir through a fifth channel to a drainage reservoir, wherein the excess of the third fluid is drained via a hydrostatic pressure differential between the output reservoir and the drainage reservoir.

In some embodiments, a first length of the first channel and a second length of the second channel are substantially equal.

In some embodiments, the first fluid and the second fluid are the same type of fluid.

In some embodiments, the same type of fluid comprises one or more reagents. In some embodiments, the same type of fluid has a contact angle of greater than about 60° and less than about 90°.

In some embodiments, (b) comprises directing the third fluid to come in contact with a fourth fluid, wherein the fourth fluid comprises the first fluid and the second fluid and a plurality of particles. In some embodiments, the plurality of particles comprises a plurality of biological particles. In some embodiments, the plurality of biological particles includes cells or derivatives thereof. In some embodiments, the plurality of particles comprises a plurality of particles having coupled thereto a plurality of barcodes.

In some embodiments, a given droplet of the plurality of droplets includes a given biological particle from the plurality of biological particles and/or a given particle having coupled thereto a given barcode of the plurality of barcodes. In some embodiments, the method further comprises, subsequent to (c), subjecting nucleic acid molecules derived from the given biological particle to nucleic acid sequencing. In some embodiments, the method further comprises, subsequent to (c), subjecting the given droplet to nucleic acid amplification conditions to yield amplification products of the nucleic acid molecules derived from the given biological particle. In some embodiments, the method further comprises subjecting the amplification products to nucleic acid sequencing.

In another aspect, provided is a system for generating a plurality of droplets, comprising: a fluid flow path comprising a first channel, a second channel, a third channel, a fourth channel, a fifth channel fluidically connecting an output reservoir and a drainage reservoir, and an intersection of the first channel and the second channel; a fluid flow unit that is configured to (i) subject a first fluid to flow along the first channel and a second fluid to flow along the second channel to the intersection, (ii) subject a third fluid to flow along the third channel to the intersection or a location downstream of the intersection, and (iii) subject a plurality of droplets to flow along the fourth channel to the output reservoir; and a controller operatively coupled to the fluid flow unit, wherein the controller is programmed to direct the fluid flow unit to subject the first fluid to flow along the first channel towards the intersection, the second fluid to flow along the second channel towards the intersection, the third fluid to flow along the third channel to the intersection or the location downstream of the intersection, and the plurality of droplets to flow along the fourth channel to the output reservoir, wherein the third fluid is immiscible with the first fluid and the second fluid, thereby generating the plurality of droplets upon the first fluid and the second fluid coming in contact with the third fluid, wherein an excess of the third fluid is drained from the output reservoir to the drainage reservoir through the fifth channel, wherein the excess of the third fluid is drained via a hydrostatic pressure differential between the output reservoir and the drainage reservoir.

In some embodiments, the fluid flow unit subjects the third fluid to come in contact with a fourth fluid at the intersection or at the location downstream of the intersection, wherein the fourth fluid comprises the first fluid and the second fluid and a plurality of particles. In some embodiments, the plurality of particles comprises a plurality of biological particles and/or a plurality of particles having coupled thereto a plurality of barcodes.

In some embodiments, the fluid flow unit includes at least one pump that is configured to provide negative pressure. In some embodiments, the fluid flow unit includes at least one compressor that is configured to provide positive pressure. In some embodiments, the fluid flow unit includes an actuator.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 8A shows a device with a microfluidics channel network configuration with an earlier fluid merging junction. FIG. 8B shows a microfluidics channel network configuration with a later fluid merging junction.

FIG. 11A shows another example of a device with a microfluidics channel network configuration. FIG. 11B shows a magnified view of a droplet generating channel structure of the microfluidics channel network configuration of FIG. 11A.

FIG. 13A shows another example of a device with a microfluidics channel network configuration. FIG. 13B shows a magnified view of a product splitting junction of the microfluidics channel network configuration of FIG. 13A.

DETAILED DESCRIPTION

Figure 1:
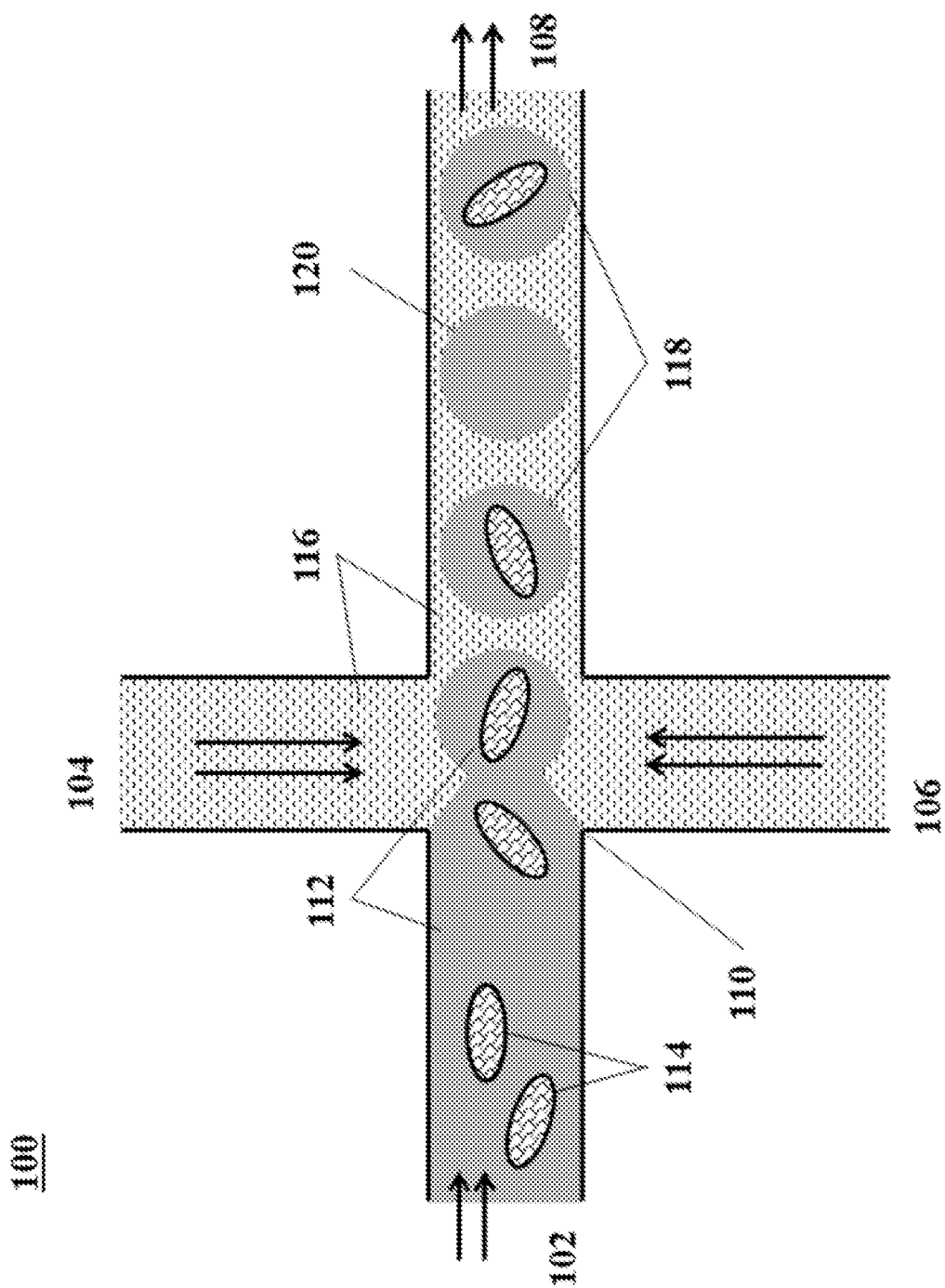
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. The subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient.

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The bead may be formed of a polymeric material. The bead may be magnetic or non-magnetic. The bead may be rigid. The bead may be flexible and/or compressible. The bead may be disruptable or dissolvable.

The term "sample," as used herein, generally refers to a biological sample of a subject. The biological sample may comprise any number of macromolecules, for example, cellular macromolecules. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within a biological particle. The macromolecular constituent may comprise a nucleic acid. The macromolecular constituent may comprise DNA. The macromolecular constituent may comprise RNA. The RNA may be messenger RNA (mRNA), ribosomal RNA (rRNA) or transfer RNA (tRNA). The RNA may be a transcript. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

Provided are microfluidics systems, devices, and networks for generating partitions. The microfluidics systems, devices, and networks may facilitate efficient merging of one or more channels in a microfluidic network and prevent blockage of a channel segment, such as by gas (e.g., air) bubbles or by one or more particles in a fluid. It may be beneficial to merge one or more wells and/or channel segments when introducing additional inputs, such as gel beads, cell beads, and/or one or more reagents into partitions. For example, single cell copy number variation (CNV) assays may require an additional well for cell beads, and so the inputs for a sample may be distributed between two adjacent layouts. A single droplet generator may receive input from wells from two or more layouts. It may be beneficial to merge one or more wells and/or channel segments when larger input volumes are required, such as to generate a greater number of partitions (e.g., droplets) and/or generate partitions with greater volume. The microfluidics channel networks provided herein may have configurations that stabilize the fluid flow dynamics of the one or more fluids communicating in the channel networks.

In an aspect, the systems and methods described herein provide for the compartmentalization, depositing, or partitioning of macromolecular constituent contents of individual biological particles into discrete compartments or partitions (referred to interchangeably herein as partitions), where each partition maintains separation of its own contents from the contents of other partitions. The partition can be a droplet in an emulsion. A partition may comprise one or more other partitions.

A partition of the present disclosure may comprise biological particles and/or macromolecular constituents thereof. A partition may comprise one or more gel beads. A partition may comprise one or more cell beads. A partition may include a single gel bead, a single cell bead, or both a single cell bead and single gel bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described further below. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can comprise droplets of aqueous fluid within a non-aqueous continuous phase (e.g., oil phase). The partitions can comprise droplets of a first phase within a second phase, wherein the first and second phases are immiscible. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual biological particles to discrete partitions may in one non-limiting example be accomplished by introducing a flowing stream of biological particles in an aqueous fluid into a flowing stream of a non-aqueous fluid, such that droplets are generated at the junction of the two streams. By providing the aqueous stream at a certain concentration and/or flow rate of biological particles, the occupancy of the resulting partitions (e.g., number of biological particles per partition) can be controlled. Where single biological particle partitions are used, the relative flow rates of the immiscible fluids can be selected such that, on average, the partitions may contain less than one biological particle per partition, in order to ensure that those partitions that are occupied are primarily singly occupied. In some cases, partitions among a plurality of partitions may contain at most one biological particle (e.g., bead, cell or cellular material). In some embodiments, the relative flow rates of the fluids can be selected such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying biological particles, cell beads, and/or gel beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
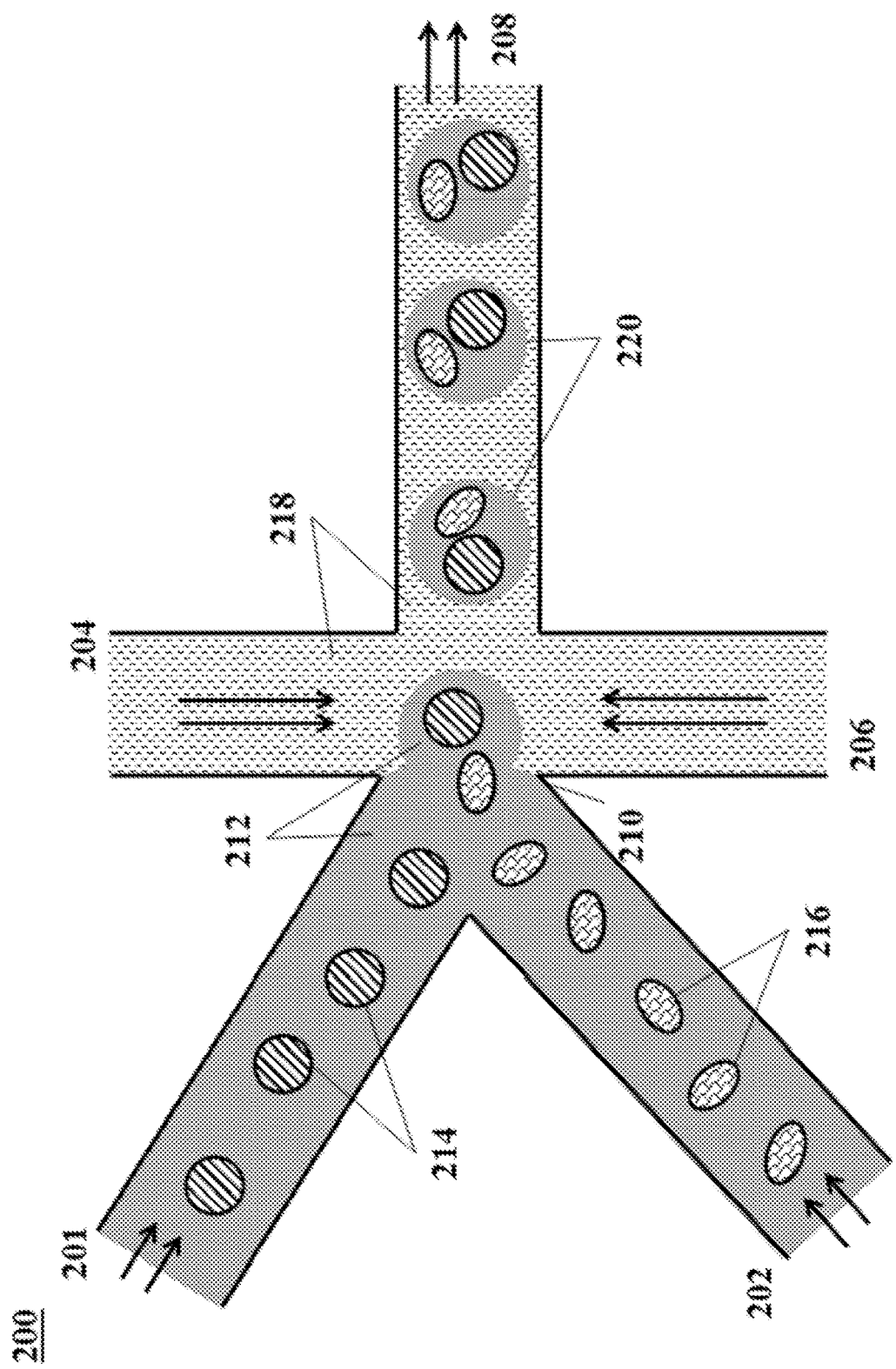
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (either heating or cooling), photo-stimuli (e.g., through photo-curing), chemical stimuli (e.g., through crosslinking, polymerization initiation of the precursor (e.g., through added initiators), or the like, and/or a combination of the above.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. In some cases, barcoded nucleic acid molecules can be initially associated with the microcapsule and then released from the microcapsule upon application of a stimulus which allows the nucleic acid molecules to dissociate or to be released from the microcapsule. A microcapsule, in some instances, can comprise a bead. Beads are described in further detail below.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 1 micrometers 5 µm, 10 µm, 20 µm, 30 µm, 40 µm, 50 µm, 60 µm, 70 µm, 80 µm, 90 µm, 100 µm, 250 µm, 500 µm, 1 mm, or greater. In some cases, a bead may have a diameter of less than about 5 µm, 10 µm, 20 µm, 30 µm, 40 µm, 50 µm, 60 µm, 70 µm, 80 µm, 90 µm, 100 µm, 250 µm, 500 µm, 1 mm, or less. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or a one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100, 000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), 3-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
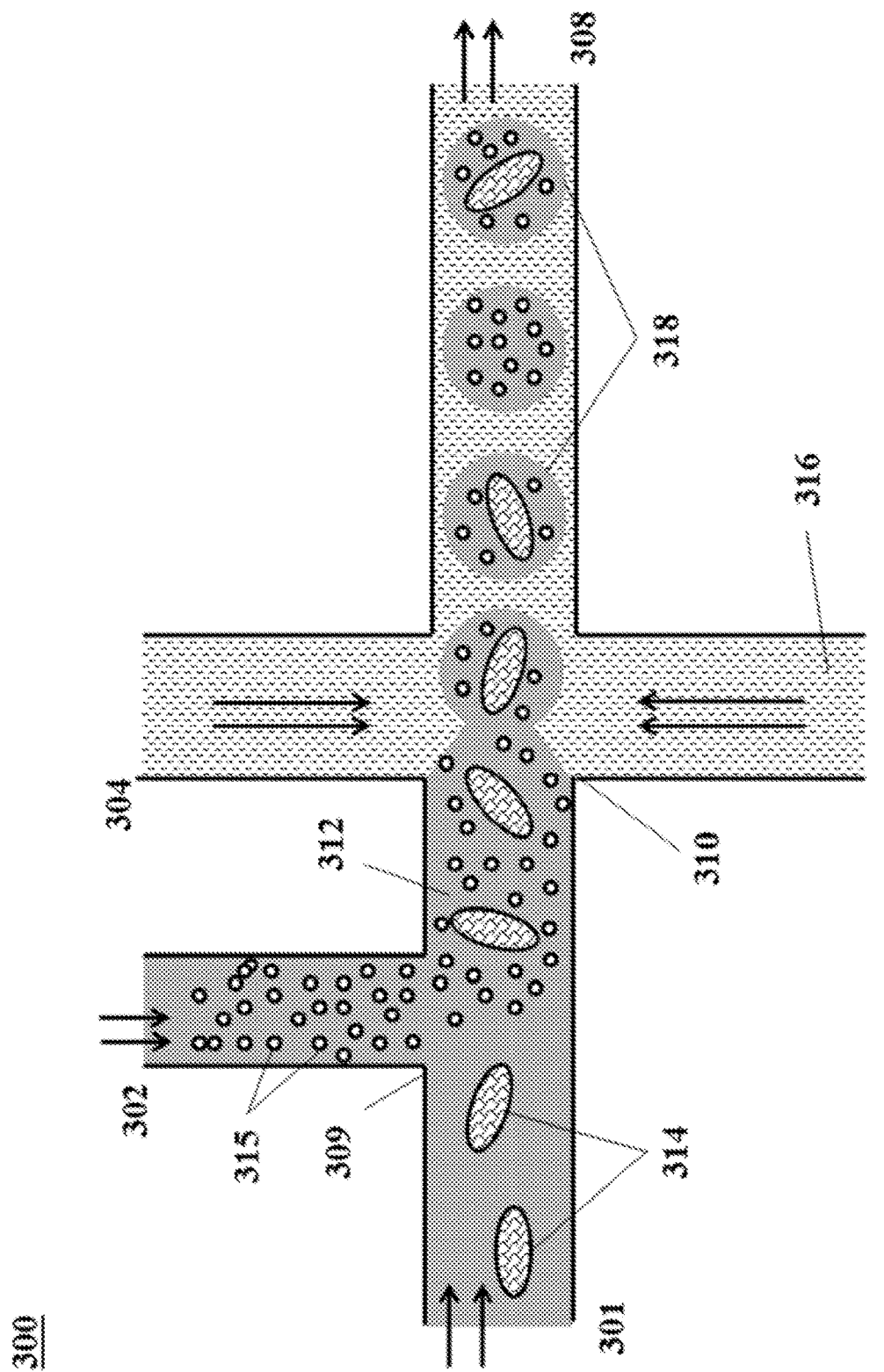
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particles' contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

In addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particle, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
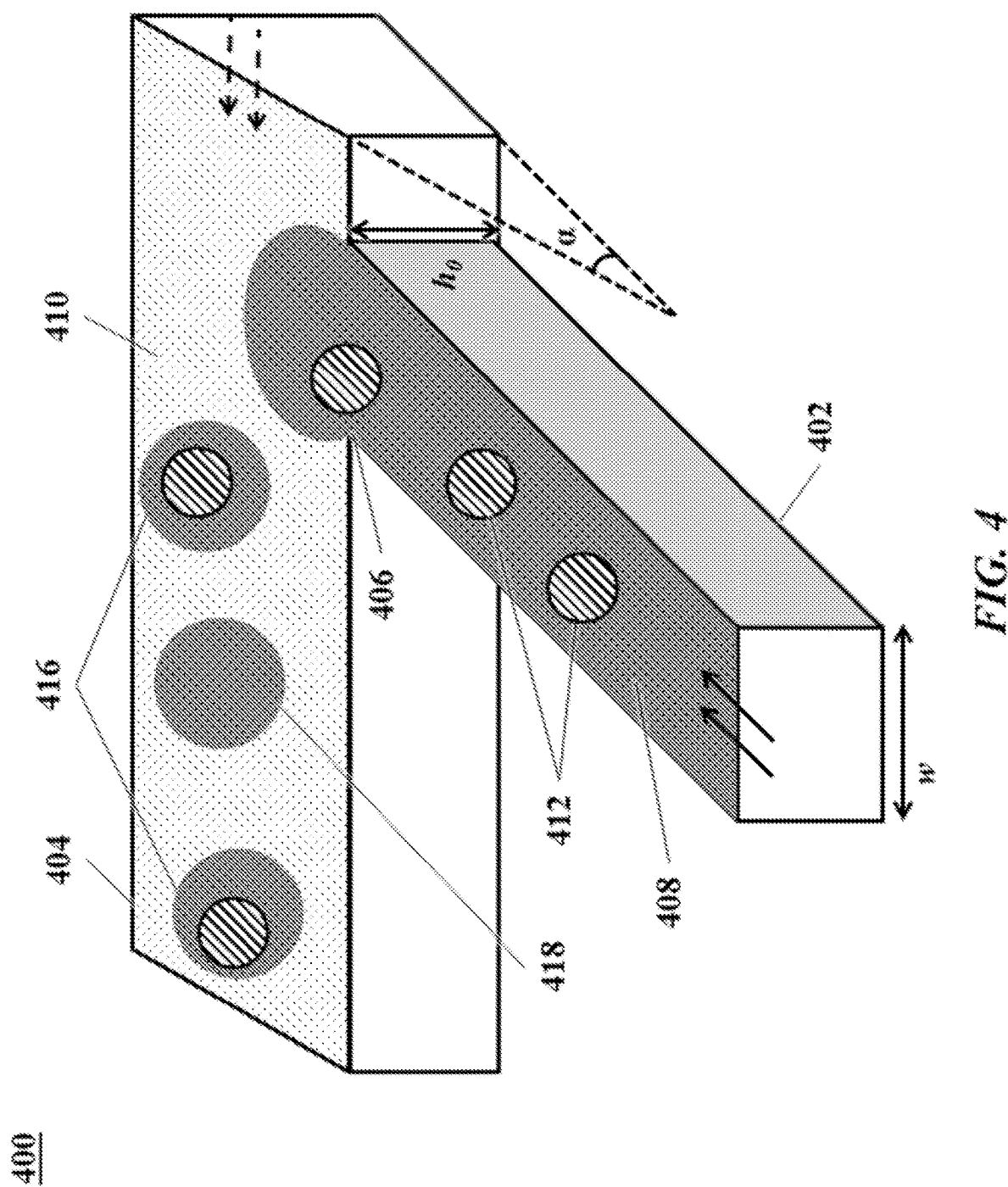
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, $\alpha$, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400.

The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, α. The expansion angle, α, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and α:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, α, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
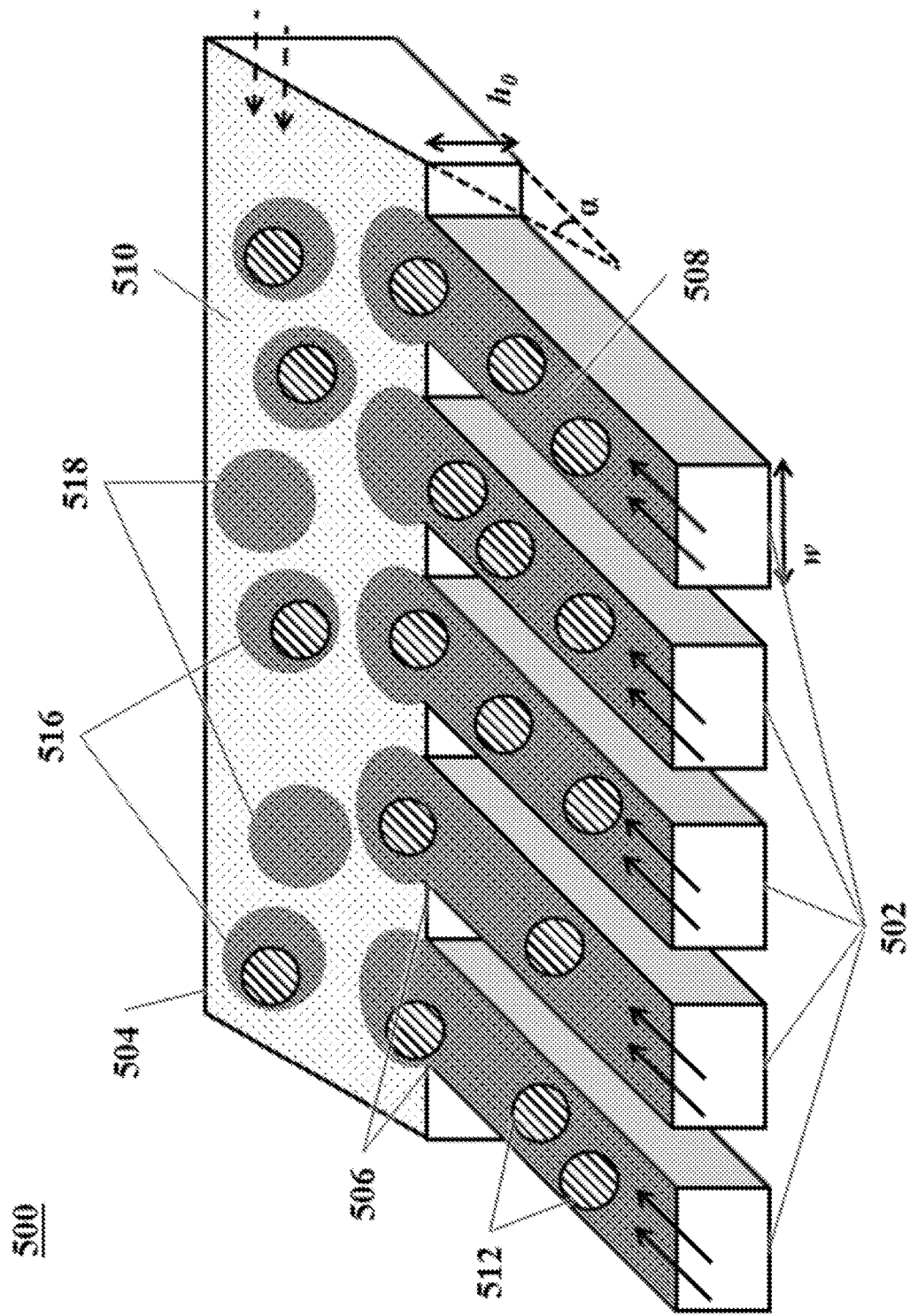
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, α, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
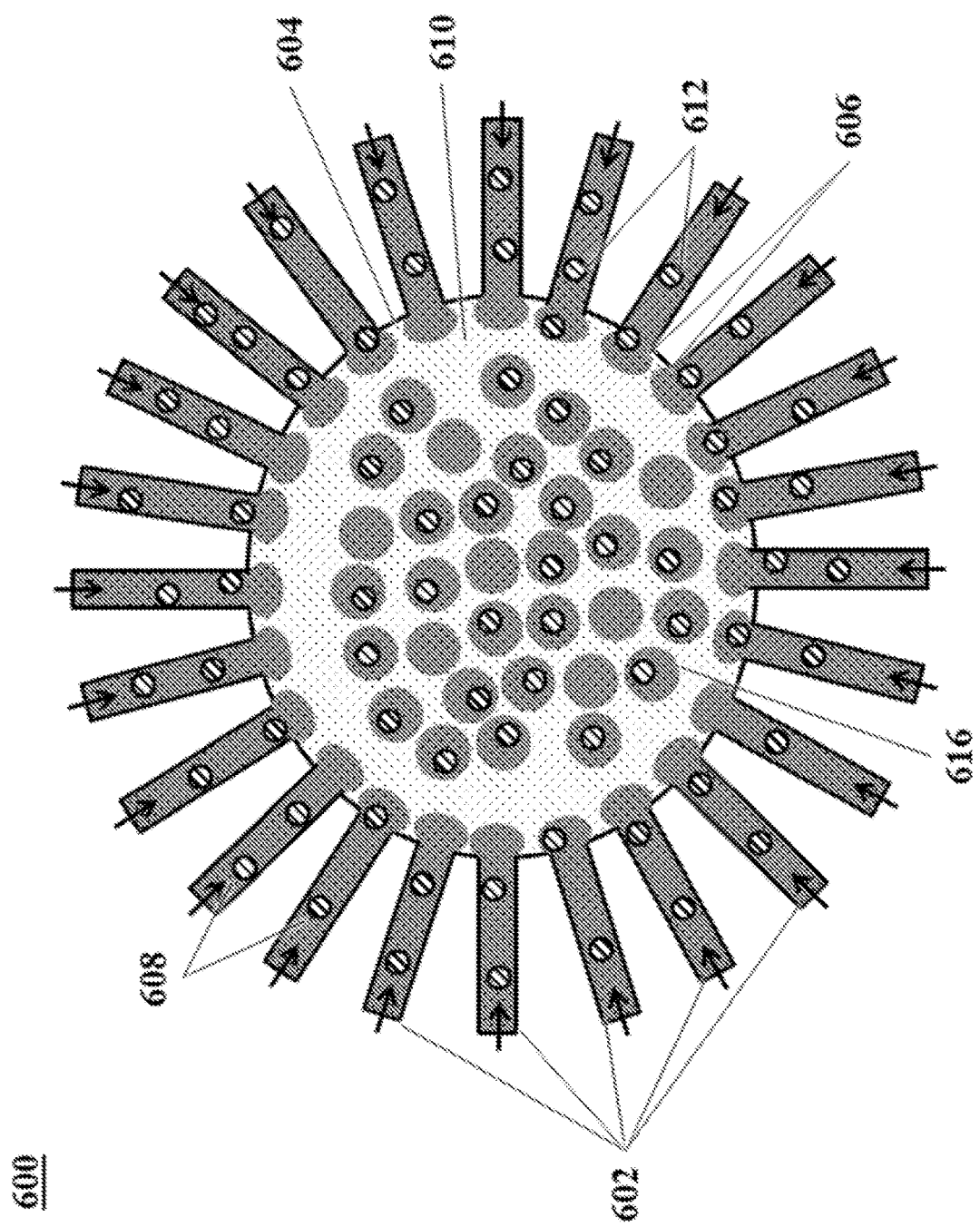
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_0$, at or near the channel junction. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

In another aspect, provided are microfluidics devices, microfluidics systems, and microfluidics channel networks for enhanced partitioning of fluids. A microfluidics system may comprise one or more microfluidics devices and/or one or more microfluidics channel networks. A microfluidics device may comprise a chip or microchip. The microfluidics device may comprise one or more microfluidics channel networks, and/or parts thereof. The microfluidics device, microfluidics system, and/or microfluidics channel network may be used to generate the partitions (e.g., droplets) described elsewhere herein. The partitions may comprise one or more beads comprising one or more barcodes and/or one or more biological particles comprising biological samples (e.g., DNA, RNA, cells, etc.). The partitions may comprise cell beads, gel beads, and/or reagents. The microfluidics channel networks may comprise and/or connect one or more channel segments, reservoirs, chambers, wells, and/or other fluidic components. Such fluidic components may be internal to the device (e.g., on chip) or external to the device (e.g., off chip). A microfluidics channel network may comprise an inlet channel and an outlet channel. Such inlet channels and/or outlet channels may be referred to herein as fluid ports. A microfluidics channel network may comprise a plurality of inlet channels and/or a plurality of outlet channels. The microfluidics channel network provided herein may facilitate the merging of one or more channel segments.

The microfluidics system and/or device may comprise a fluid flow unit. A microfluidics channel network may be operatively coupled to the fluid flow unit. The fluid flow unit may comprise a pressure source, such as a vacuum pump configured to be a source of negative pressure and/or a positive pressure pump configured to be a source of positive pressure. The fluid flow unit may comprise both a positive pressure source and a negative pressure source. For example, the pumps may be diaphragm pumps, syringe pumps, rotary pumps, or other pumps. The fluid flow unit may comprise a compressor. In some instances positive pressure and/or negative pressure may be applied via one or more ports (e.g., fluid inlet channels, fluid outlet channels). The microfluidics system and/or device may comprise one or more valves. The valve may be a one-way valve, two-way valve, three-way valve, four-way valve, or other type of valve. The valve may be a bypass valve. The valve may be an on/off valve. The valve may be continuously adjustable. The valve may be operatively coupled to one or more fluidics devices, such as channel segments and/or other fluid flow paths (e.g., connected to a pressure source, connected to a vent, etc.). The microfluidics system and/or device may comprise one or more sensors (e.g., pressure sensors, optical sensors, electrical sensors, etc.).

The fluid flow units, valves and/or sensors may be operatively coupled to one or more controllers that are, individually or collectively, configured to control and operate the microfluidics system and/or device. In some instances, the controller may be capable of receiving feedback (e.g., sensor data) from and/or controlling the fluid flow units, valves and/or sensors. The controller may be part of a control system, such as described further below. The controller may be operatively coupled to a user interface configured to allow user input. The user interface may comprise an auditory or graphical user interface (e.g., display, screen, touchscreen, touchpad, lights, etc.). The user interface may comprise one or more user interactive devices, such as buttons, levers, knobs, keys, keyboards, mouse, joysticks, keypads, touchscreens, data ports, microphones, cameras, or other devices. The controller may be operatively coupled to output devices, such as a display, screen, printer, data port, speaker, light bulb, or the like.

Figure 7:
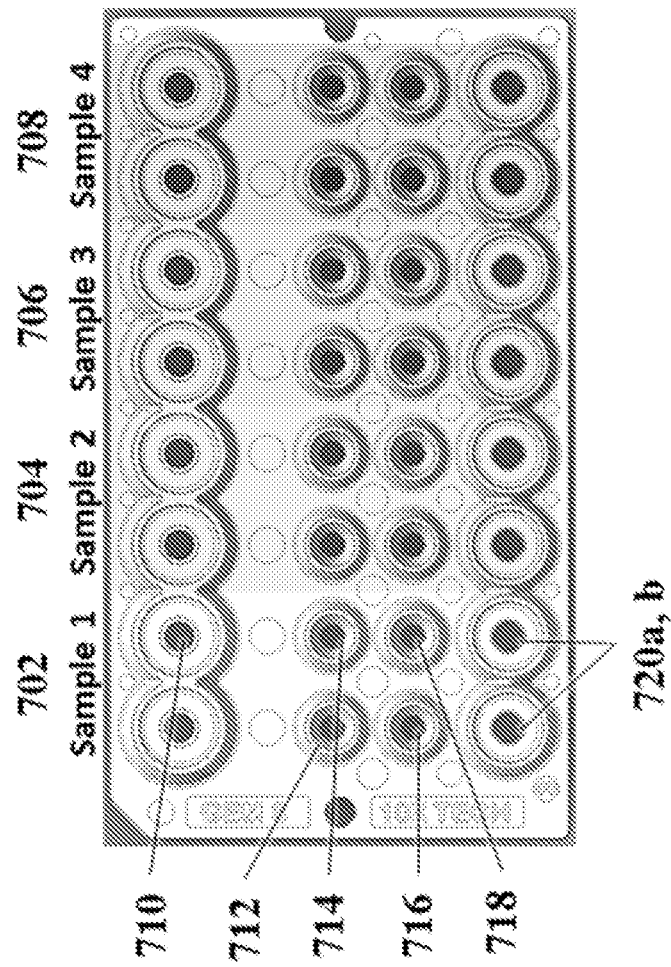
FIG. 7 shows a microfluidics device comprising microfluidics channel networks.

FIG. 7 shows a microfluidics device 700 comprising microfluidics channel networks. The device 700 may be a chip or a microchip. The device 700 may facilitate processing of a first sample 702, a second sample 704, a third sample 706, and a fourth sample 708. While only four samples are illustrated, a single device may facilitate processing of more samples, such as 5, 6, 7, 8, 9, 10, 15, 20, 25, 30, 35, 40, 45, 50, or more samples. As will be appreciated, the dimensions (e.g., length, width, depth, layers) of the chip may increase to accommodate more samples. In some cases, each sample may be processed independent of other samples on the device 700. In some cases, different samples may each be processed via one or more isolated microfluidics channel networks. Alternatively, different samples may be processed using one or more fluids (e.g., oil, reagent) from a same source (e.g., reservoir, well, channel segment, etc.).

For example, the one or more fluids may be in fluid communication via one or more microfluidics channel networks.

The first sample 702 may be processed via a microfluidics channel network comprising a first well 710, a second well 712, a third well 714, a fourth well 716, a fifth well 718, and a sixth and seventh well 720a, b. A well may be a reservoir or chamber. A well may be a channel segment. A well may be a channel inlet and/or outlet. For example, a well may be an inlet well (interchangeably, an input well). A well may be an outlet well (interchangeably, an output well). While a particular number of wells are illustrated in FIG. 7, there can be any number of wells on a chip, such as 1, 2, 3, 4, 5, 6, 7, 8, 9, 10, 20, 30, 40, 50, 100, 150, 200, 300, 400, 500, or more wells. While a specific ordered array of wells are illustrated in FIG. 7, the wells may be arranged in any configuration, such as in any number of rows and columns, in single file, or arbitrarily. In some instances, the wells may be spaced according to standard well-to-well microplate spacing configurations (e.g., center-to-center spacing of about 18 millimeters (mm), 9 mm, 4.5 mm, 2.25 mm, or 1.125 mm). Alternatively, the wells may be spaced arbitrarily. The plurality of wells may have the same sizes or different sizes. In some instances, the plurality of wells may have the same sizes by row or by column. The plurality of wells may have the same shapes or different shapes. In some instances, the plurality of wells may have the same shapes by row or by column. The plurality of wells may be substantially coplanar, or a subset of the plurality of wells may be substantially coplanar. In some instances, the wells may not be coplanar. In some instances, one or more wells may be inclined. In some instances, one or more wells may be tapered, such as to have different cross-section diameters (or other cross-section dimensions) at different heights or depths.

Discrete inputs and outputs for the processing of the first sample 702 may be distributed between the plurality of wells 710-720a,b. The plurality of wells may be adjacent. The plurality of wells may be non-adjacent. The plurality of wells may be in fluid communication via one or more microfluidics channel networks. The first well 710 may comprise emulsion products, for example, droplets (e.g., aqueous-in-non-aqueous) and partitioning fluid. The first well 710 may be an outlet well. The second well 712 may comprise gel beads. The third well 714 may comprise cell beads. The fourth well 716 and fifth well 718 may comprise reagents. The sixth and seventh wells 720a, b may comprise a partitioning fluid, such as oil. The partitioning fluid may be immiscible with an aqueous fluid. The wells 712-720a, b may be inlet wells. In some instances, each well may be in fluid communication with a channel segment. One or more channel segments may be in fluid communication or networked via one or more microfluidics channel networks. Via the one or more microfluidics channel networks, a plurality of wells 712-720a, b may be merged to generate one or more droplets in oil, such as in the first well 710. Systems and methods of droplet generation are described elsewhere herein, for example with respect to FIGS. 1-6. For example, each input well (e.g., 712-720a, b) may correspond to a source of a fluid (e.g., aqueous fluid, a fluid immiscible with the aqueous fluid, a fluid comprising cell beads, a fluid comprising gel beads, a fluid comprising reagents, a fluid comprising biological particles, etc.) in one or more channel segments. For example, the output well (e.g., 710) may correspond to a reservoir or chamber for collecting, storing, and/or intermediately transporting the generated droplets. The generated droplets may comprise the gel beads, the cell beads, and/or the reagents.

It may be beneficial to merge one or more wells and/or channel segments when introducing additional inputs, such as gel beads, cell beads, and/or one or more reagents into partitions. It may be beneficial to merge one or more wells and/or channel segments when larger input volumes are required, such as to generate a greater number of partitions (e.g., droplets) and/or generate partitions with greater volume. Provided are microfluidics channel networks that operatively merge one or more wells and/or channel segments for partitioning. The microfluidics channel networks may have configurations that stabilize the fluid flow dynamics of the one or more fluids communicating in the channel networks. For example, the devices, systems and networks may prevent gas (e.g., air) bubbles from being trapped in the network, facilitate uniformity of droplet size, facilitate monodispersity of occupied droplets (e.g., singularly occupied droplet), prevent contamination, such as from undesired or untimely merging of two or more fluids, and effectively drain excess fluids (e.g., oil).

FIGS. 8A and 8B show microfluidics channel network configurations. FIG. 8A shows a microfluidics channel network configuration 800A with an earlier fluid merging junction 808. FIG. 8B shows a microfluidics channel network configuration 800B with a later fluid merging junction 818.

In a first network configuration 800A, a first set of wells 802 may each comprise oil (or other partitioning fluid), a second well 804 may comprise a first input fluid (e.g., reagent), and a third well 806 may comprise a second input fluid (e.g., reagent). The first input fluid and the second input fluid may be the same or different liquid. In some instances, the first set of wells 802 may correspond to the sixth and seventh wells 720a, b, the second well 804 may correspond to the fourth well 716, and the third well 806 may correspond to the fifth well 718.

An input fluid (e.g., liquid), such as water, oil, or a reagent solution may have different wetting properties, which may vary with the different adhesive and cohesive properties of the input liquid. A contact angle ($\theta$), or the angle at which the liquid-vapor interface of the input liquid meets the solid-liquid interface of the input liquid, may be indicative of such wetting properties. A liquid may be more wetting as the contact angle approaches 0° and less wetting as the contact angle approaches 180°. While liquids such as oil may readily wick into the microfluidics channel network, such that oil from each of the first set of wells 802 merge at a first fluid merging junction 803 to combine without substantial disruption or disturbance in the flow of fluid, some liquids that are only slightly wetting, such as one or more reagents described elsewhere herein (e.g., first input liquid and second input liquid), may flow from a source well to fill or flow into a channel segment with varying speeds, such that when a slower-filling channel segment and a faster-filling channel segment merges at a second fluid merging junction 808 that is too close to the inlet well (e.g., source of the liquid), one or more gas (e.g., air) bubbles may be trapped in the slower-filling channel segment. For example, such slightly wetting liquids may have a contact angle from between about 60° to about 90°. For example, the slightly wetting liquids may have a contact angle of about 60°, 65°, 70°, 75°, 80°, 85°, or 90°. Alternatively, the slightly wetting liquids may have a contact angle lower than 60° or greater than 90°. Slightly wetting liquids may have different filling speeds due to varying surface chemistry, surface roughness heterogeneity, other surface properties and/or other fluid properties.

For example, when the wells 804, 806 are filled with liquid sequentially, and the merging junction 808 is too close to the inlet well(s), the liquid from the well that is filled first can flow into the entrance channel of the second well and begin to fill the bottom of the second well. When liquid is then added to the second well, volumes of gas (e.g., air bubbles) may be trapped between the two liquid volumes, such that when pressure is applied at both wells, the volumes of gas trapped in the second well is compressed and dissipates the pressure drop, or is pinned by geometric features, and cannot be flushed out through the channels.

Trapped gas (e.g., air) bubbles can block a channel segment and prevent liquid in a well (e.g., second well 804, third well 806) from flowing into the microfluidics channel network, or otherwise reduce a rate at which such liquid can enter the microfluidics channel network, rendering the volume of input liquid in the well unavailable or difficult to access or predict for the generation of emulsions (e.g., droplets). For example, in the first network configuration 800A, the first input liquid from the second well 804 and/or the second input liquid from the third well 806 may be a slightly wetting liquid, such that the first input liquid fills a channel segment at a slower rate than the second input liquid. When the two input liquids merge at or near the second fluid merging junction 808 that is too close to the second well 804 and/or third well 806, gas (e.g., air) bubbles may be trapped in the channel segment connected to the second well 804, preventing the first input liquid from entering the microfluidics channel network. In the example illustrated in FIG. 8A, the length of a channel from an input well to the merging junction 808 may be less (or substantially less) than the length of a downstream channel leading away from the merging junction 808.

In a second network configuration 800B, a second fluid merging junction 818 is located more downstream than the second fluid merging junction 808 of the first second network configuration 800A, such that there is greater distance between the merging junction and each of the input wells 814, 816. The second network configuration 800B may comprise a first set of wells 812 which may each comprise oil, a second well 814 comprising a first input fluid (e.g., reagent), and a third well 816 comprising a second input fluid (e.g., reagent). The first input fluid and the second input fluid may be the same or different liquid. In some instances, the first network configuration 800A and constituents thereof may correspond to the second network configuration 800B and constituents thereof, excluding the different location of the second fluid merging junction 818. Oil from each of the first set of wells 812 may merge at a first fluid merging junction 813 to combine without substantial disruption or disturbance in the flow of fluid.

The first input liquid from the second well 814 and/or the second input liquid from the third well 816 may be a slightly wetting liquid, such that the first input liquid fills a channel segment at a slower rate than the second input liquid. The channel segment carrying the first input liquid from the second well 814 and the channel segment carrying the second input liquid from the third well 816 may merge at the second merging junction 818. The distance between either the second well 814 or the third well 814 and the second merging junction 818 in the second network configuration 800B may be greater than the distance between either the second well 804 or the third well 806 and the second merging junction 808 in the first network configuration 800A. Beneficially, in the second network configuration 800B, the filling of the respective channel segments from the second well 814 and the third well 816 may stabilize, or have stabilized, over the greater distance that is travelled in the channel segments to reach the second merging junction 808. For example, at or near the second merging junction 808, the respective fluids (e.g., first input liquid, second input liquid) in each of the merging channel segments may be at the same, or substantially the same, filling rate. The second merging junction 808 may be located at a distance from either of the two wells such that the liquids merge without substantial disruption or disturbance (e.g., trapping of air bubbles). In some instances, the distance from the second well 814 to the second merging junction 808 and the distance from the third well 816 to the second merging junction 808 may be substantially the same. Alternatively, the distance from the second well 814 to the second merging junction 808 and the distance from the third well 816 to the second merging junction 808 may be different. However, the distance may be selected such that issues with trapped gas (e.g., air) are reduced, if not eliminated. For example, the greater distance from the merging junction 808 to the respective wells can allow more time for liquid from both wells to flow into the microfluidics device, such as before one channel is blocked by fluid from the other. The extent of filling may also even out over the greater distance. In some instances, passive valves may be located upstream of the merging junction 808 to help even out the fluid flow. In the example illustrated in FIG. 8B, the length of a channel from an input well to the merging junction 818 may be greater (or substantially greater) than the length of a downstream channel leading away from the merging junction 818. For example, the difference in lengths may be at least about 0.001 millimeters (mm), 0.01 mm, 0.1 mm, 1 mm, 10 mm or more.

The configuration may be applied to the merging of any two channel segments of fluids, including water, oil, reagent solutions, fluids comprising gel beads, cell beads, and/or biological particles, and/or fluids comprising other particles (e.g., suspended particles). The configuration may be applied to merging of three or more channel segments.

Figure 9:
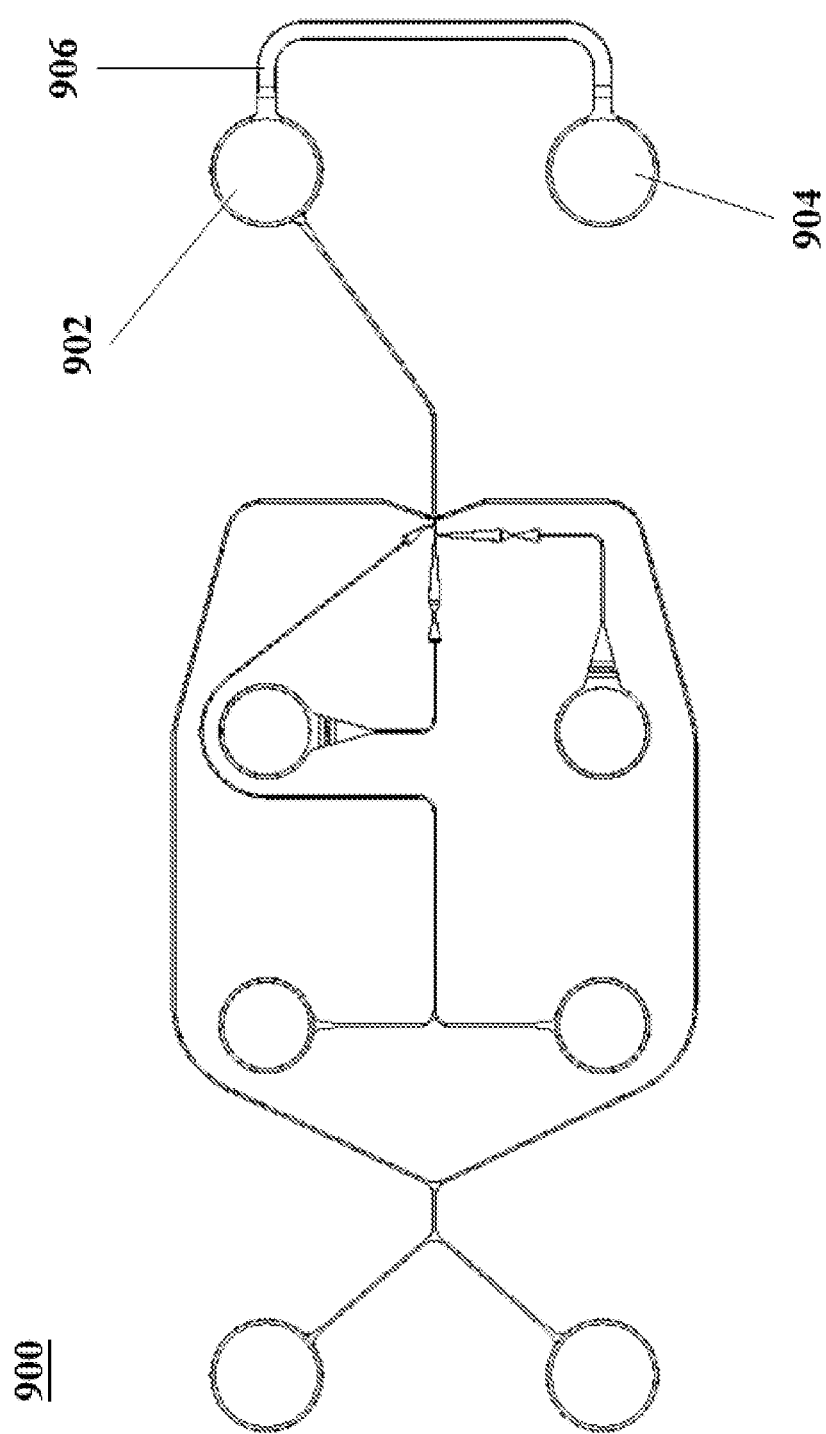
FIG. 9 shows another example of a device with a microfluidics channel network configuration.

FIG. 9 shows another example of a microfluidics channel network configuration. In some cases, a network configuration 900 and constituents thereof may correspond to the first network configuration 800A or the second network configuration 800B. The network configuration 900 may comprise an emulsion well 902, a drainage well 904, and a shunt 906. The emulsion well 902 may comprise emulsion products, such as described elsewhere herein. The emulsion products may comprise one or more discrete partitions (e.g., droplets) in a partitioning fluid (e.g., oil). In some instances, the emulsion products may comprise excess partitioning fluid, such as to achieve primarily singularly occupied droplets (e.g., beads, biological particles, cell beads, etc.) and/or monodispersity, as described elsewhere herein. The emulsion well 902 may be in fluid communication with the drainage well 904 via the shunt 906. In some instances, excess partitioning fluid (e.g., excess oil) may be directed from the emulsion well 902 to the drainage well 904 through the shunt 906. The excess partitioning fluid may be directed (or recycled) from the drainage well 904 to a source of the partitioning fluid (e.g., at least one well of the first set of wells 802 or 812 of FIG. 8A or 8B, respectively). A hydrostatic pressure differential between the liquid levels in the two wells 902, 904 may subject the excess partitioning fluid to drain from the emulsion well 902 to the drainage well 904. The partitions (e.g., droplets) may have a lower density than that of the partitioning fluid. The partitions may have a rise rate that is sufficiently faster than the drainage flow rate, such as to avoid entrainment in the drainage flow. The drainage well 904 may be drained to adjust a liquid level to influence the hydrostatic pressure differential between the two wells 902, 904. Beneficially, the shunt 906 may obviate the need for pushback. In some instances, a plurality of emulsion wells 902 may be in fluid communication with the same drainage well 904, such as via separate shunts, and the excess partitioning fluid may drain in response to a combined hydrostatic pressure differential between the liquid levels in the plurality of emulsion wells and the drainage well.

In some instances, the emulsion well 902 may be in fluid communication with a plurality of shunts 906 to a plurality of drainage wells 904. For example, this configuration can increase the extent of draining if a greater excess of partitioning fluid was used, such that there may still be excess partitioning fluid present in the emulsion well 902 after the hydrostatic pressure is equilibrated in a system with a single drainage well.

As can be appreciated, the diameter and/or shape of the interior of the respective wells may be varied to control the amount of partitioning fluid that is drained from the emulsion well. For example, a larger diameter may drain more partitioning fluid until the hydrostatic pressure is equilibrated.

As can be appreciated, the dimensions of the shunt 906 may be varied to control the rate of drainage. The dimensions of the shunt may be varied to control the rate of drainage to be less than the rise rate of the partitions in the partitioning fluid. In some instances, the shunt may have a cross-section dimension (e.g., diameter, width, height, etc.) of about 200 micrometers ($\mu$m) to about 500 $\mu$m. The cross-section dimension, as used herein, may refer to a dimension normal to the axis of flow direction of the shunt. In some instances, the cross-section dimension of the shunt 906 may taper as the shunt 906 nears a well (e.g., 902, 904). The shunt may have a cross-section dimension of at least about 100, 110, 120, 130, 140, 150, 160, 170, 180, 190, 200, 210, 220, 230, 240, 250, 300, 350, 400, 450, 500, 550, 600 $\mu$m or more. In some instances, the shunt may have a cross-section dimension of at most about 600, 550, 500, 450, 400, 350, 300, 250, 240, 230, 220, 210, 200, 190, 180, 170, 160, 150, 140, 130, 120, 110, 100 $\mu$m or less.

In some instances, the resistance of the shunt 906 may be varied to control the rate of drainage, and/or of the back-flow (from the drainage well to the emulsion well) that may occur when the emulsion is removed from the emulsion well. In an example, a high shunt resistance may be favored in cases where the emulsion is removed from the bottom of the emulsion well, to prevent the aspiration of oil that has flowed back from the drainage well and into the emulsion well, in place of the emulsion. In another example, a low shunt resistance may be favored in cases where layouts are combined to make a greater number of partitions or larger partitions, to prevent over-filling the emulsion well during the generation of emulsion.

Figure 15:
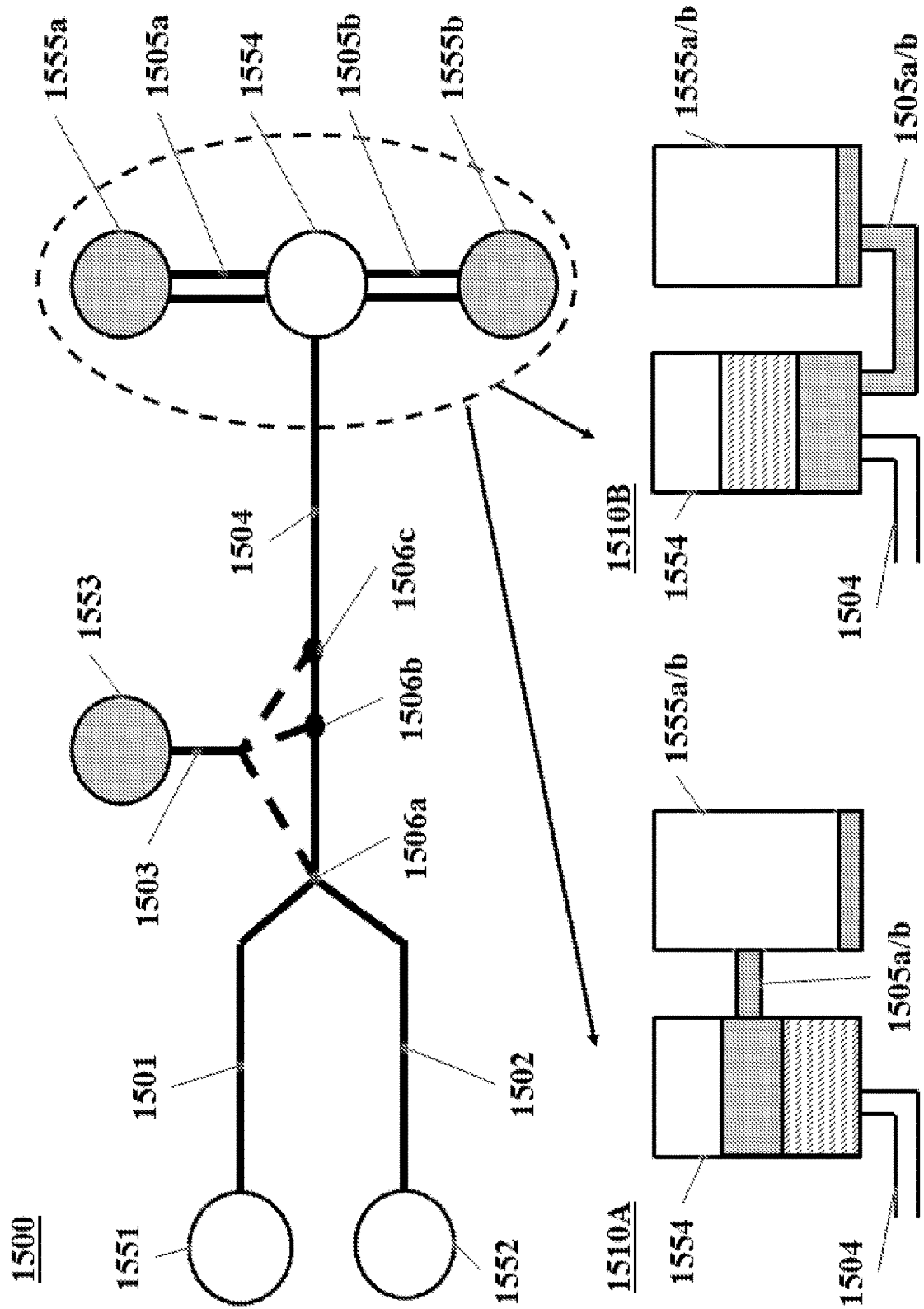
FIG. 15 shows another example of a microfluidics channel network configuration with multiple drainage reservoirs.

In some instances, a network may have two or more drainage reservoirs. FIG. 15 shows another example of a microfluidics channel network configuration with multiple drainage reservoirs. In some cases, a network configuration 1500 and constituents thereof may correspond to the first network configuration 800A or the second network configuration 800B or the network configuration 900. The network configuration 1500 may comprise a first input well 1551, a second input well 1552, a partitioning fluid well 1553, an emulsion well 1554, a first drainage well 1555a, and a second drainage well 1555b. The first input well 1551 and a second input well 1552 may comprise a first input fluid (e.g., reagent) and a second input fluid (e.g., reagent), respectively, as described elsewhere herein. The partitioning fluid well 1553 may comprise a partitioning fluid, such as oil, as described elsewhere herein. The emulsion well 1554 may comprise emulsion products, as described elsewhere herein. The emulsion well 902 may be in fluid communication with the first drainage well 1555a via a first drainage channel 1505a and in fluid communication with the second drainage well 1555b via a second drainage channel 1505b.

The emulsion products may comprise one or more discrete partitions (e.g., droplets) in a partitioning fluid (e.g., oil). In some instances, the emulsion products may comprise excess partitioning fluid, such as to achieve primarily singularly occupied droplets (e.g., beads, biological particles, cell beads, etc.) and/or monodispersity, as described elsewhere herein. In some instances, excess partitioning fluid (e.g., excess oil) may be directed from the emulsion well 1554 to the first drainage well 1555a and/or the second drainage well 1555b via the first drainage channel 1505a and 1505b, respectively. In some instances, a hydrostatic pressure differential between the liquid levels in the two wells 1554, 1555a may subject the excess partitioning fluid to drain from the emulsion well 1554 to the first drainage well 1555a. Similarly, a hydrostatic pressure differential between the liquid levels in the two wells 1154, 1555b may subject the excess partitioning fluid to drain from the emulsion well 1554 to the second drainage well 1555b. The drainage to the multiple drainage wells (e.g., 1555a, 1555b) may be simultaneous. The partitions may have a rise rate that is sufficiently faster than the drainage flow rate, such as to avoid entrainment in the drainage flow. The drainage wells 1555a, b may be drained to adjust their liquid levels to influence the hydrostatic pressure differentials between the emulsion well 1554 and the drainage wells 1555a, b. Beneficially, the drainage channel 1505(a or b) may obviate the need for pushback. In some instances, the excess partitioning fluid may be directed (or recycled) from the drainage well(s) to a source of the partitioning fluid (e.g., 1553).

In some instances, the partitions (e.g., droplets) may have a higher density than that of the partitioning fluid, as illustrated in a cross-sectional side view schematic 1510A of a portion of network 1500, and the drainage channel 1505a/b may be located at a first (higher) level in the emulsion well 1554 such as to allow the partitioning fluid emulsified above the partitions to drain at the first (higher) level. For example, the drainage channel may be located at or above a predetermined threshold level. In some instances, the partitions may have a lower density than that of the partitioning fluid, as illustrated in a cross-sectional side view schematic 1510B of a portion of network 1500, and the drainage channel 1505a/b may be located at a second (lower) level in the emulsion well 1554 such as to allow the partitioning fluid emulsified below the partitions to drain at the second (lower) level. For example, the drainage channel may be located at or below a predetermined threshold level.

As can be appreciated, the diameter and/or shape of the interior of the respective wells (e.g., emulsion well 1554, first drainage well 1555a, second drainage well 1555b) may be varied to control the amount of partitioning fluid that is drained from the emulsion well. For example, a larger diameter may drain more partitioning fluid until the hydrostatic pressure is equilibrated.

As can be appreciated, the dimensions of the drainage channels 1505a, b may be varied to control the rate of drainage. The dimensions may be varied to control the rate of drainage to be less than the rise rate of the partitions in the partitioning fluid. In some instances, a drainage channel may have a cross-section dimension (e.g., diameter, width, height, etc.) of about 200 micrometers (μm) to about 500 μm. The cross-section dimension, as used herein, may refer to a dimension normal to the axis of flow direction of the drainage channel. In some instances, the cross-section dimension of the drainage channel may taper as the drainage channel nears a well. The drainage channel may have a cross-section dimension of at least about 100, 110, 120, 130, 140, 150, 160, 170, 180, 190, 200, 210, 220, 230, 240, 250, 300, 350, 400, 450, 500, 550, 600 μm or more. In some instances, the drainage channel may have a cross-section dimension of at most about 600, 550, 500, 450, 400, 350, 300, 250, 240, 230, 220, 210, 200, 190, 180, 170, 160, 150, 140, 130, 120, 110, 100 μm or less.

As can be appreciated, the number of drainage channels and/or drainage wells may be varied to control the drainage rate. For example, there may be at least about 2, 3, 4, 5, 6, 7, 8, 9, 10, 11, 12, 13, 14, 15, 16, 17, 18, 19, 20 or more drainage channels from the emulsion well 1554. For example, there may be at least about 2, 3, 4, 5, 6, 7, 8, 9, 10, 11, 12, 13, 14, 15, 16, 17, 18, 19, 20 or more drainage wells in fluidic communication with the emulsion well 1554.

In some instances, the resistance of the drainage channels 1505a, b may be varied to control the rate of drainage, and/or of the back-flow (from a drainage well to the emulsion well) that may occur when the emulsion is removed from the emulsion well. In an example, a high resistance may be favored in cases where the emulsion is removed from the bottom of the emulsion well, to prevent the aspiration of oil that has flowed back from the drainage well and into the emulsion well, in place of the emulsion. In another example, a low resistance may be favored in cases where layouts are combined to make a greater number of partitions or larger partitions, to prevent over-filling the emulsion well during the generation of emulsion.

FIG. 15 further illustrates different merging configurations between input well(s) and the partitioning fluid well. The network 1500 illustrates two input wells 1551, 1552, but there may be any number of input wells. For example, there may be a single input well (e.g., comprising aqueous fluid). In another example, there may be three or more input wells. The multiple input wells may merge at a single junction or different multiple junctions. As an example, the network 1550 illustrates a first input fluid from the first input well 1551 traveling along a first input channel 1501 and a second input fluid from the second input well 1552 traveling along a second input channel 1502 to merge at a first junction 1506a. The partitioning fluid may merge at the same junction that other input fluids merge at, or alternatively, at a different junction (with an already merged fluid). For example, the partitioning fluid from the partitioning fluid well 1553 may travel along a partitioning fluid channel 1503 to merge at the first junction 1506a where the two other input fluids merge, or at a second junction 1506b or third junction 1506c to merge with an already merged fluid (of the two other input fluids). The partitioning fluid may merge at any junction located along channel 1504.

Figure 10:
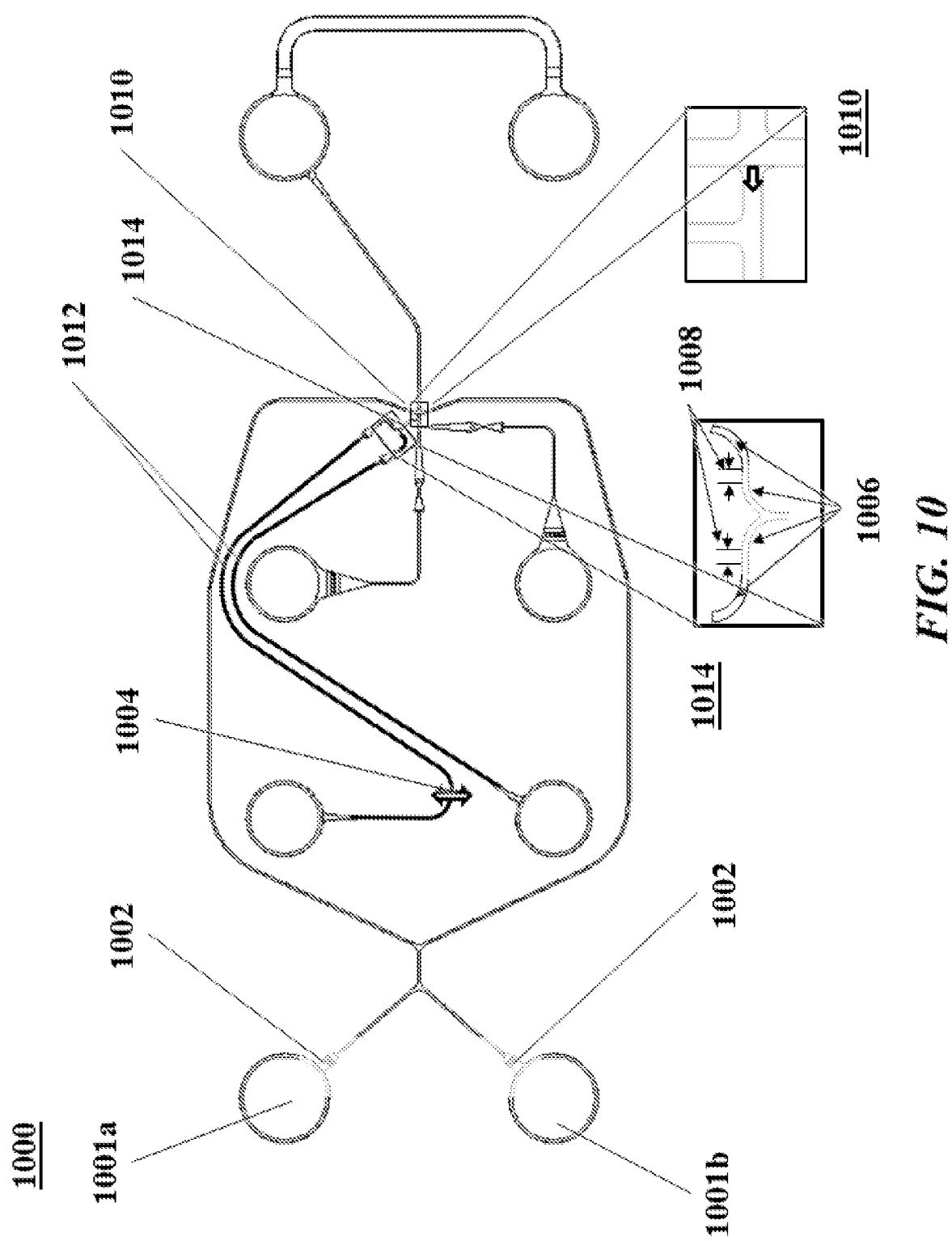
FIG. 10 shows another example of a device with a microfluidics channel network configuration.

FIG. 10 shows another example of a microfluidics channel network configuration. In some cases, a network configuration 1000 and constituents thereof may correspond to the second network configuration 800B and/or the network configuration 900.

The network configuration 1000 may comprise a first oil well and a second oil well 1001a, b. The first oil well and second oil well may each comprise oil. Alternatively, the well can comprise another partitioning fluid (e.g., continuous phase in an emulsion). Each oil well may be in fluid communication with its own channel segment. The channel segment may be configured to carry oil from the oil well to, for example, an intersection with one or more other channel segments (e.g., merging junction 803, 813). For example, the respective channel segments from the first oil well and the second oil well may carry oil to an oil merging junction, where the oil fluids are combined, which combined oil can then be transported to a droplet generating junction (e.g., see droplet generating channel structure 1010). In some instances, an oil filter 1002 may be disposed between the oil wells 1001a, b and the respective channel segments. In some instances, a reverse passive valve may be disposed upstream or downstream of the oil filter 1002.

As described with respect FIG. 8B, two channel segments 1012 each sourcing fluid respectively from two input fluid wells (e.g., reagent wells) may merge at a merging junction 1014, wherein the merging junction 1014 is located at a sufficient distance from one or both input fluid wells, such as to prevent the forming of gas (e.g., air) bubbles (e.g., due to varying channel filling rates). In some instances, the length of the channel segments from the respective input well to the merging junction 1014 can be substantially the same. The term "length," as used herein, generally refers to the linear or non-linear distance from a first point to a second point along a channel or channel segment. For example, in a linear channel segment having an input and an output, the length of the channel segment is the linear distance from the input to the output. As another example, in a serpentine channel segment having an input and an output, the length is the non-linear distance from the input to the output. In some instances, the length of a channel segment having an input and an output can refer to the distance a fluid molecule travels from the input to the output of the channel segment. In some instances, the length of a channel segment having an input and an output can refer to the shortest or longest distance a fluid molecule travels from the input to reach the output of the channel segment. For example, a first of the two channel segments may be configured to trace one or more curves 1004 to adjust the length of the first channel to be substantially equal to the length of a second of the two channel segments. The one or more curves 1004 may be adjusted, or one or more curves added or subtracted, to substantially equalize the length of the two channel segments. Alternatively or in addition, the second of the two channel segments may be configured to trace one or more curves to adjust length. As will be appreciated, depending on the available chip area and locations for one or both channel segments, the path and/or configuration of the channel segments may be adjusted accordingly. In some instances, other channel segments in the microfluidics channel network 1000 may be adjusted or moved to accommodate the two channel segments 1012. Beneficially, the substantially equal length of the two channel segments may increase the likelihood that a first fluid from a first channel does not enter a second channel (in which a second fluid is flowing).

In some instances, the respective lengths of the two channel segments may be different by at most about 10 millimeters (mm), 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, 0.009 mm, 0.008 mm, 0.007 mm, 0.006 mm, 0.005 mm, 0.004 mm, 0.003 mm, 0.002 mm, 0.001 mm or less.

Alternative to or in addition to substantially equalizing the length of the two channel segments, one or more fluid pinning features may be disposed in one or both channels before the merging junction 1014. Alternative to or in addition to substantially equalizing the length of the two channel segments, one or more frictional or non-frictional elements may be disposed in or configured (designed) into one or both channels before the merging junction 1014. For example, such frictional elements may increase cohesive forces between a fluid and the channel to affect the flow rate. In another example, such frictional elements (e.g., a decrease in cross-section diameter, a texture or pattern in the channel wall, a protrusion, etc.) may disrupt the flow of the fluid to affect the flow rate. In another example, a non-frictional element (e.g., a coating) may decrease cohesive forces between a fluid and the channel. Beneficially, the same benefits (e.g., increase the likelihood that a first fluid from a first channel does not enter a second channel (in which a second fluid is flowing)) may be achieved without coordinating the lengths of the channels to be substantially the same.

The two channel segments 1012 may have the same or different cross-section dimensions. In an example, each channel segment may have a cross-section dimension of about 75 µm. Alternatively or in addition, one or both channel segments may have a cross-section dimension of at least about 15, 20, 25, 30, 35, 40, 45, 50, 55, 65, 70, 75, 80, 85, 90, 95, 100, 105, 110, 115, 120 µm or more. Alternatively or in addition, one or both channel segments can have a cross-section dimension of at most about 120, 115, 110, 105, 100, 95, 90, 85, 80, 75, 70, 65, 55, 50, 45, 40, 35, 30, 25, 20, 15 µm or less. The two channel segments 1012 may have a minimum edge-to-edge spacing of about 350 µm. Alternatively or in addition, the minimum edge-to-edge spacing may be at least about 300, 310, 320, 330, 340, 350, 360, 370, 380, 390, 400, 450, 500, 550, 600 µm or greater. Alternatively, the minimum edge-to-edge spacing may be less than about 350 µm.

Referring to the blown up illustration of the merging channel junction 1014, the two channel segments 1012 can each follow an 'S' shaped path with a curvature radius 1006 of about 80 µm (for the two curves in the 'S' shape) and intervening linear length 1008 (between the two curves of the 'S' shape) of about 50 µm. After the second curve, the two channel segments 1012 may intersect with the other to form a curve with an intersection curvature radius of about 40 µm. Alternatively, the dimensions may be different. For example, the curvature radius 1006 can be at least about 40, 45, 50, 55, 65, 70, 75, 80, 85, 90, 95, 100, 105, 110, 115, 120 µm or more. Alternatively or in addition, the curvature radius 1006 can be at most about 120, 115, 110, 105, 100, 95, 90, 85, 80, 75, 70, 65, 55, 50, 45, 40 µm or less. In another example, the intervening linear length 1008 can be at least about 30, 35, 40, 45, 50, 55, 65, 70, 75, 80, 85, 90, 95, 100, 105, 110, 115, 120 µm or more. Alternatively or in addition, the intervening linear length 1008 can be at most about 120, 115, 110, 105, 100, 95, 90, 85, 80, 75, 70, 65, 55, 50, 45, 40, 35, 30 µm or less. The intersection curvature radius can be at least about 15, 20, 25, 30, 35, 40, 45, 50, 55, 65, 70, 75, 80, 85, 90, 95, 100, 105, 110, 115, 120 µm or more. Alternatively or in addition, the intersection curvature radius can be at most about 120, 115, 110, 105, 100, 95, 90, 85, 80, 75, 70, 65, 55, 50, 45, 40, 35, 30, 25, 20, 15 µm or less.

The merged oil (or other partitioning fluid), and the merged reagents (or other input fluids, such as aqueous fluids, fluids carrying particles (e.g., gel beads, cell beads, biological particles, etc.), may communicate via a droplet generating channel structure 1010. For example, the droplet generating channel structure 1010 may correspond to the microfluidic channel structure 300 in FIG. 3. The droplet generating channel structure 1010 may correspond to any other microfluidic channel structures described herein, such as with respect to FIGS. 1-6.

FIG. 11A shows another example of a microfluidics channel network configuration. FIG. 11B shows a magnified view of a droplet generating channel structure of the microfluidics channel network configuration of FIG. 11A. In some cases, a network configuration 1100 and constituents thereof may correspond to other network configurations (e.g., 800A, 800B, 900, 1000) described herein, and constituents thereof. In some cases, a droplet generating channel structure 1100A of the network configuration 1100 may correspond to other droplet generating channel structures described herein, such as the droplet generating channel structure 1010, the microfluidic channel structure 300, or other microfluidic channels structures described herein, such as with respect to FIGS. 1-6.

Provided are exemplary dimensions for the network configuration 1100 to generate a plurality of droplets, each droplet comprising about 2.2 nanoliters (nL) in volume, with an aqueous:partitioning (e.g., oil) fluid ratio of about 0.6. A first channel segment 1104a may source a partitioning fluid (e.g., oil) from a first partitioning fluid well. A second channel segment 1104b may source the partitioning fluid from a second partitioning fluid well. In some instances, the first channel segment 1104a and the second channel segment 1104b may have the same, or substantially the same lengths. A cross-section dimension of each of the first and second channel segments 1104a-b may be from about 80 µm to about 125 µm. The length of the each segment 1104a, 1104b can be about 0.5 millimeters (mm). The partitioning fluid from the first and second channel segments 1104a-b may merge into a third channel segment 1104c, which can then split back into a fourth channel segment 1104d and a fifth channel segment 1104e. In some instances, the fourth channel segment 1104d and the fifth channel segment 1104e may have the same, or substantially the same lengths. A cross-section dimension of each of the fourth and fifth channel segments 1104d-e may be about 125 µm. The partitioning fluid from each of the fourth and fifth channels segments 1104d-e may come in fluid communication at a droplet generating junction (see FIG. 11B), for example to meet an aqueous fluid comprising one or more particles (e.g., gel beads, cell beads, reagents, biological particles, etc.).

A sixth channel segment 1103a may source a first input fluid (e.g., reagent) from a first input well. A seventh channel segment 1103b may source a second input fluid (e.g., reagent) from a second input well. The first input fluid and the second input fluid may be the same or different input fluid. For example, the first input fluid and the second input fluid may comprise the same reagent (e.g., lysis agent). In some instances, the sixth channel segment 1103a and the seventh channel segment 1103b may have the same, or substantially the same lengths. A cross-section dimension of each of the sixth and seventh channel segments 1103a-b may be about 65 µm. The first input fluid and the second liquid fluid from the sixth and seventh channel segments 1103a-b, respectively, may merge into eighth channel segment 1103c. The merging junction (e.g., intersection of channel segments 1103a-c) may be located at a distance from the first input well and/or the second input well such that filling speeds of the two channel segments 1103a-b are substantially equal and/or merging does not disturb fluid flow in the network configuration 1100 (e.g., by trapped air bubbles). The merged first and second input fluid may travel along the eighth channel segment 1103c towards the droplet generation junction. In some instances, the eighth channel segment 1103c may merge with one or more other channel segments at the partitioning junction. In some instances, the eighth channel segment 1103c may merge with one or more other channel segments upstream (e.g., immediately upstream or shortly upstream) of the partitioning junction, such as to merge with an aqueous fluid comprising one or more particles before being partitioned together at the partitioning junction, as described elsewhere herein.

A ninth channel segment 1101 may source a third input fluid from a third input well. A tenth channel segment 1102 may source a fourth input fluid from a fourth input well. In some instances, the third input fluid may be an aqueous fluid comprising a plurality of a first type of particles (e.g., cell beads). In some instances, the fourth input fluid may be an aqueous fluid comprising a plurality of a second type of particles (e.g., gel beads). The third and/or fourth input fluid may comprise a plurality of types of particles. The third or fourth input fluid may comprise the same or different types of particles. For example, the third input fluid and fourth input fluid may both be an aqueous fluid comprising gel beads. The ninth channel segment 1101 and the tenth channel segment 1102 may direct the third input fluid and the fourth input fluid, respectively, to the droplet generating channel structure 1100A. In some instances, the ninth channel segment 1101 and the tenth channel segment 1102 may have the same, or substantially the same lengths. A cross-section dimension of each of the ninth and tenth channel segments 1101-2 may taper from about 80 µm to about 65 µm. The cross-section dimension of about 80 µm, for example, may reduce susceptibility to clogging of the channel segments with dimer/trimer gel beads (or other particles). In some instances, the cross-section dimension of a channel segment may allow one or more particles in the aqueous fluid to flow in single file along the channel segment. In some instances, the curvature at which the ninth channel segment 1101 exits the third input well may be adjusted. In some instances, the curvature at which the tenth channel segment 1102 exits the fourth input well may be adjusted.

A fluid network can include flow regulators for providing a substantially regular flow of fluid through a channel. The flow regulator can be disposed in the channel, upstream of the channel or downstream of the channel. The channel can include at least 1, 2, 3, 4, 5, 6, 7, 8, 9, 10, or more flow regulators.

A flow regulator can have a cross-section that is greater than a general cross-section (e.g., diameter) of a channel. Such cross-section can increase along a general direction of fluid flow and taper to the general cross-section of the channel. The flow regulator can be integrated with the channel, such as a unitary or single piece element of the channel (e.g., injection molded as a single piece). For example, the ninth channel segment 1101 and tenth channel segment 1102 each comprises two flow regulators. Each flow regulator has a cross-section that widens along the general direction of flow. The flow regulators may have different cross-section profiles or the same cross-section profiles. Alternatively or in addition, the ninth channel segment 1101 and/or the tenth channel segment 1102 may each have 1, 2, 3, 4, 5, 6, 7, 8, 9, 10, or more flow regulators.

FIG. 11B illustrates the droplet generating channel structure 1100A of the network configuration 1100. As can be seen, the ninth channel segment 1101 and the tenth channel segment 1102 may merge at a first intersection, thereby merging the third input fluid and the fourth input fluid. Downstream of the first intersection, the eighth channel segment 1103c may merge with the merge with the merged stream of the third input fluid and the fourth input fluid at a second intersection, thereby merging the third input fluid and the fourth input fluid with the first input fluid and the second input fluid. Downstream of the second intersection, the merged stream of the first-fourth input fluids may merge with the fourth channel segment 1104d and the fifth channel segment 1104e at a third intersection, thereby merging the merged stream of the first-fourth input fluids with the partitioning fluid, which is immiscible to the first-fourth input fluids, to generate a plurality of partitions (e.g., droplets). The third intersection can be the partitioning junction. Each partition may comprise the first input fluid, second input fluid, third input fluid, and/or the fourth input fluid. Emulsion products, such as the plurality of partitions and the partitioning fluid, may be directed along an outlet channel segment to an outlet well. In some instances, the outlet channel segment may have a cross-section dimension of about 125 µm. The outlet well may be in fluid communication with a drainage well via a shunt 1105. The shunt 1105 may correspond to the shunt 906 with respect to FIG. 9. In some instances, the center of the drainage well and a longitudinal axis (e.g., direction of primary flow) of the shunt may have a distance of about 3.5 mm. In some instances, prior to the partitioning junction, the channel segments in the droplet generating structure may have a cross-section diameter of about 65 µm. In some instances, prior to a fluid in a channel segment merging with another fluid, for example, at the first intersection, the second intersection, and/or the third intersection, the channel segment may be substantially linear (e.g., with a length of the linear portion of at least about 143 µm or about 182 µm). Exemplary dimensions of the droplet generating structure 1100A are illustrated in FIG. 11B. The resulting droplets may have a volume of about 2.2 nL.

As will be appreciated, the network configuration 1100 and/or droplet generating structure 1100A may be adjusted accordingly to generate droplets comprising different volumes, and/or different aqueous:partitioning fluid ratios. In some instances, a channel segment of the microfluidics channel and/or networks described herein may have a cross-section dimension from about 50 µm to about 200 µm. Alternatively in addition, a channel segment can have a cross-section dimension from at least about 50, 55, 65, 70, 75, 80, 85, 90, 95, 100, 105, 110, 115, 120, 130, 140, 150, 160, 170, 180, 190, 200 µm or more. Alternatively or in addition, a channel segment can be at most about 200, 190, 180, 170, 160, 150, 140, 130, 120, 115, 110, 105, 100, 95, 90, 85, 80, 75, 70, 65, 55, 50 µm or less.

Figures 12A, 12B:
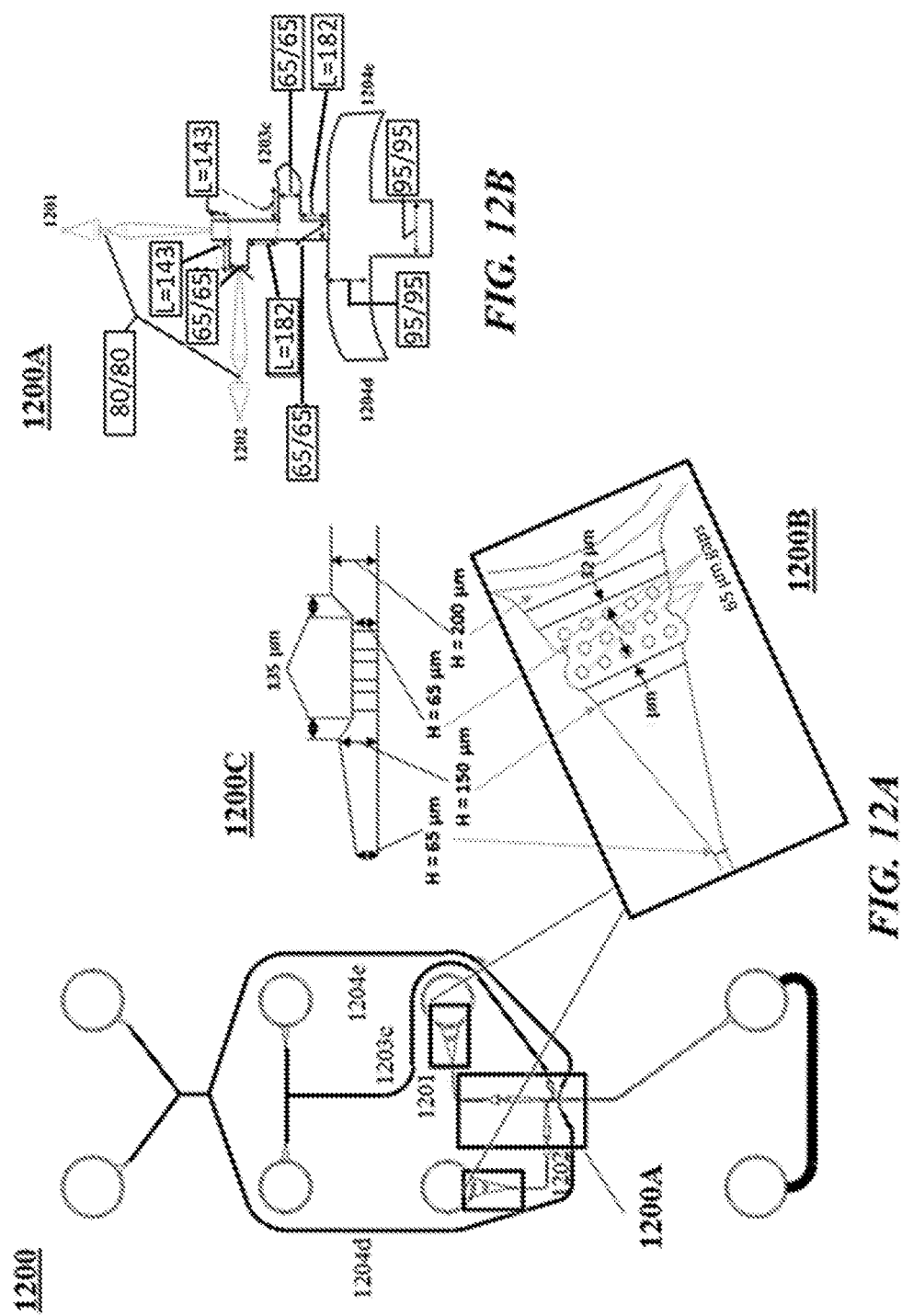
FIG. 12A shows another example of a device with a microfluidics channel network configuration.
FIG. 12B shows a magnified view of a droplet generating channel structure of the microfluidics channel network configuration of FIG. 12A.

FIG. 12A shows another example of a microfluidics channel network configuration. FIG. 12B shows a magnified view of a droplet generating channel structure of the microfluidics channel network configuration of FIG. 12A. In some cases, a network configuration 1200 and constituents thereof may correspond to other network configurations (e.g., 800A, 800B, 900, 1000, 1100) described herein, and constituents thereof. For example, the channel segment 1201 may correspond to the channel segment 1101 of FIGS. 11A-B, and the channel segment 1202 may correspond to the channel segment 1102 of FIGS. 11A-B. In some cases, a droplet generating channel structure 1200A of the network configuration 1200 may correspond to other droplet generating channel structures described herein, such as the droplet generating channel structure 1010, the droplet generating channel structure 1100A, the microfluidic channel structure 300, or other microfluidic channels structures described herein, such as with respect to FIGS. 1-6.

Provided are exemplary dimensions for the network configuration 1200 to generate a plurality of droplets, each droplet comprising about 1.1 nanoliters (nL) in volume, with an aqueous:partitioning (e.g., oil) fluid ratio of about 0.6. Some differences with the network configuration 1100 are provided. Unless otherwise distinguished, the components (and dimensions) of the network configuration 1200 may correspond to the components (and dimensions) of the network configuration 1100. For example, as shown in FIG. 12B, a cross-section dimension of each of a fourth channel segment 1204d and a fifth channel segment 1204e (each carrying partitioning fluid) may be about 95 µm. In some instances, an outlet channel segment may have a cross-section dimension of about 95 µm. A passive valve may be removed from an eight channel segment 1203c before merging downstream (e.g., at the second intersection in channel generating structure 1100A). The shunt may have a cross-section dimension of about 500 µm. In some instances, the cross-section dimension of the shunt may taper down to about 200 µm when approaching a well (e.g., outlet well, drainage well). Alternatively or in addition, the shunt may have a cross-section dimension of at least about 100, 110, 120, 130, 140, 150, 160, 170, 180, 190, 200, 210, 220, 230, 240, 250, 300, 350, 400, 450, 500, 550, 600 µm or more. In some instances, the shunt may have a cross-section dimension of at most about 600, 550, 500, 450, 400, 350, 300, 250, 240, 230, 220, 210, 200, 190, 180, 170, 160, 150, 140, 130, 120, 110, 100 µm or less.

A top view 1200B of an input well funnel is magnified from the network configuration 1200. A side view 1200C of the input well funnel is also shown. An input well, as described elsewhere herein, may comprise a fluid (e.g., aqueous fluid) comprising one or more particles such as gel beads and/or cell beads. A channel segment may source such fluid comprising one or more particles from the input well. In some instances, the funnel 1200B may be disposed between the input well and the channel segment. Alternatively or in addition the funnel 1200B may be an integral part of either the input well and/or the channel segment. Exemplary dimensions are illustrated in the top view 1200B and the side view 1200C. For example, the funnel may have a cross-section height of about 200 µm at or near the input well. This cross-section height may taper down to a pillar segment of the funnel with a cross-section height of about 65 µm. The tapering may occur over a 135 µm length of the funnel. The funnel may comprise a plurality of pillars in the pillar segment. In some instances, the pillars may be arranged in an orderly array with about 32~65 µm end-to-end gaps between the pillars. In some instances, each pillar may have a cross-section height of about 65 µm. Downstream of the pillar segment, the cross-section height of the funnel may increase to about 150 µm. In some instances, the increasing may occur gradually over a 135 µm length of the funnel. Thereafter, the funnel may taper down to a cross-section height of about 65 µm.

As will be appreciated, the network configuration 1200, the input well funnel, and/or droplet generating structure 1200A may be adjusted accordingly to generate droplets comprising different volumes, and/or different aqueous:partitioning fluid ratios. In some instances, a channel segment of the microfluidics channel and/or networks described herein may have a cross-section dimension from about 50 µm to about 200 µm. Alternatively in addition, a channel segment can have a cross-section dimension from at least about 50, 55, 65, 70, 75, 80, 85, 90, 95, 100, 105, 110, 115, 120, 130, 140, 150, 160, 170, 180, 190, 200 µm or more. Alternatively or in addition, a channel segment can be at most about 200, 190, 180, 170, 160, 150, 140, 130, 120, 115, 110, 105, 100, 95, 90, 85, 80, 75, 70, 65, 55, 50 µm or less.

FIG. 13A shows another example of a microfluidics channel network configuration. FIG. 13B shows a magnified view of a product splitting junction of the microfluidics channel network configuration of FIG. 13A. In some cases, a network configuration 1300 and constituents thereof may correspond to other network configurations (e.g., 800A, 800B, 900, 1000, 1100, 1200) described herein, and constituents thereof.

Provided are exemplary dimensions for the network configuration 1300 to generate a plurality of droplets, each droplet comprising about 1.1 nanoliters (nL) in volume, with an aqueous:partitioning (e.g., oil) fluid ratio of about 0.6. Some differences with the network configuration 1200 are provided. Unless otherwise distinguished, the components (and dimensions) of the network configuration 1300 may correspond to the components (and dimensions) of the network configuration 1200. For example, as shown in FIGS. 13A and 13B, after the partitioning junction, the outlet channel segment may direct the emulsion products (e.g., droplets in partitioning fluid) to two different outlet wells. The outlet channel segment may fluidly communicate with a first product channel segment and a second channel segment at a product splitting junction 1300B. In some instances, the product splitting junction may be a substantially T-shaped intersection. The first product channel segment may direct the emulsion products to a first outlet well and the second product channel segment may direct the emulsion products to a second outlet well. In some instances, the first product channel segment and the second channel segment may have the same, or substantially the same length. In some instances, the outlet channel segment may have a cross-section diameter of about 95 µm, and each of the first and second product channel segments can have a cross-section diameter of about 125 µm. The product splitting junction 1300 may form a curvature radius of about 200 µm between the outlet channel segment and the first product channel segment, and likewise between the outlet channel segment and the second product channel segment. After the first product channel segment curves with a curvature radius of about 200 µm upon splitting, the first product channel segment may have about 125 µm of linear length and then curve downwards with a curvature radius of about 200 µm. For example, from the outlet channel segment to the first outlet well, the first product channel segment may trace a 'S' shaped path. Likewise for the second product channel segment (e.g., tracing an 'S' shaped path in an opposite direction).

A channel segment of an input well from the network configuration 1300 is magnified in frame 1300A. An input well funnel may be disposed between the channel segment and the input well. The input well, as described elsewhere herein, may comprise a fluid (e.g., aqueous fluid) comprising one or more particles such as gel beads and/or cell beads. The channel segment may source such fluid comprising one or more particles from the input well. In some instances, the funnel may be configured in likewise manner to the funnel 1200B in network configuration 1200. Alternatively or in addition the input well funnel may be an integral part of either the input well and/or the channel segment. Exemplary dimensions of the funnel and the channel segment are illustrated in frame 1300A. For example, the funnel may have a cross-section height of about 200 µm at or near the input well. This cross-section height may taper down to a pillar segment of the funnel with a cross-section height of about 117 µm. The funnel may comprise a plurality of pillars in the pillar segment. In some instances, the pillars may be arranged in an orderly array with about 54 μm end-to-end gaps between the pillars. The channel segment may have a cross-section dimension of about 117 μm at or near the funnel. In some instances, the channel segment may have a length (e.g., in the direction of fluid flow) of about 20 mm before reaching a second funnel upstream of a merging junction (e.g., with another channel segment). The second funnel may also comprise a plurality of pillars with gaps of about 54 μm. Thereafter, the cross-section dimension of the channel segment may taper to about 65 μm. The channel segment may have a cross-section dimension of about 65 μm at or near the merging junction.

As will be appreciated, the network configuration 1300, the input well funnel, the second funnel, and/or product splitting structure 1300B may be adjusted accordingly to generate droplets comprising different volumes, and/or different aqueous:partitioning fluid ratios. In some instances, a channel segment of the microfluidics channel and/or networks described herein may have a cross-section dimension from about 50 μm to about 200 μm. Alternatively in addition, a channel segment can have a cross-section dimension from at least about 50, 55, 65, 70, 75, 80, 85, 90, 95, 100, 105, 110, 115, 120, 130, 140, 150, 160, 170, 180, 190, 200 μm or more. Alternatively or in addition, a channel segment can be at most about 200, 190, 180, 170, 160, 150, 140, 130, 120, 115, 110, 105, 100, 95, 90, 85, 80, 75, 70, 65, 55, 50 μm or less.

Figure 14:
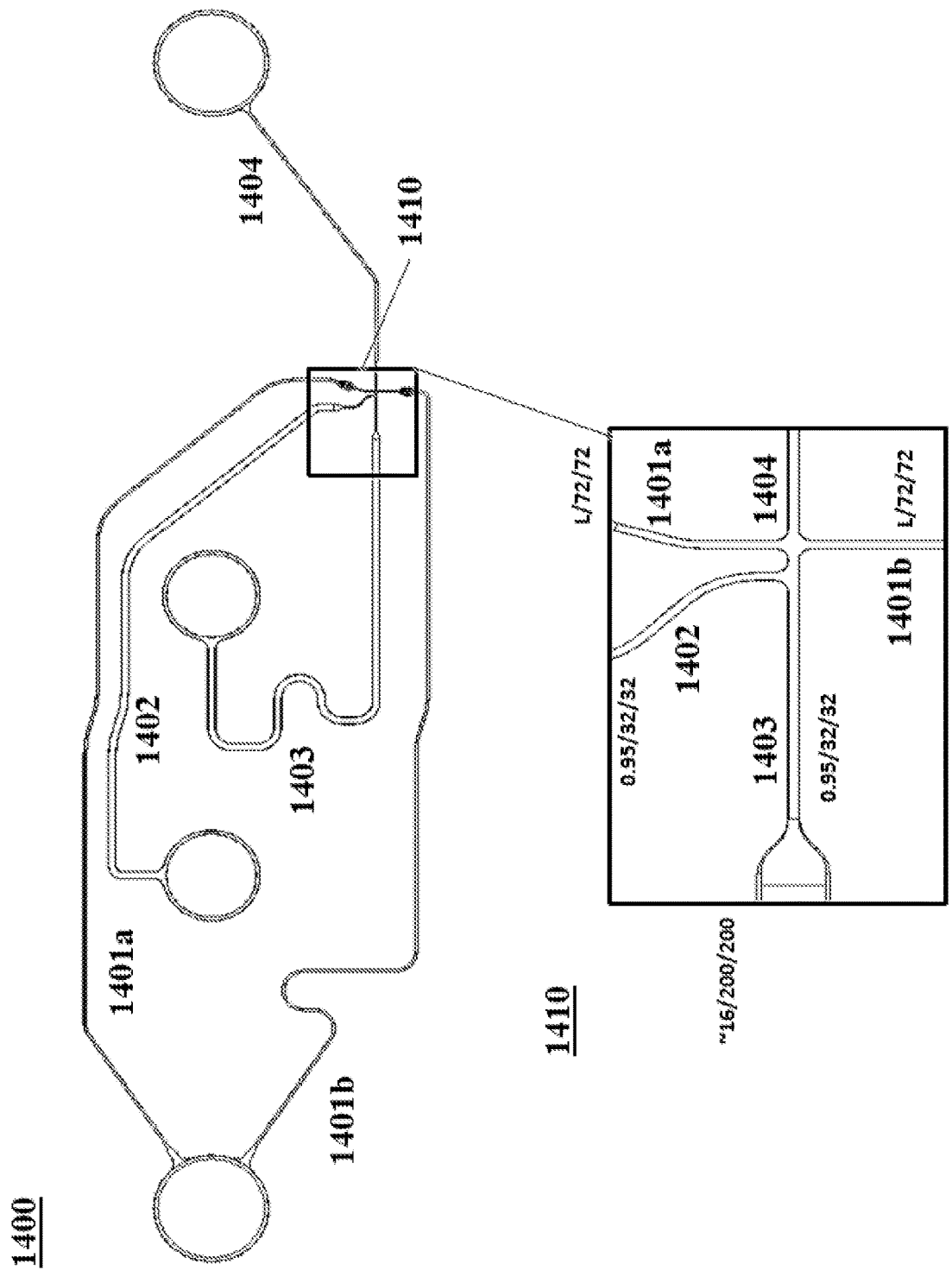
FIG. 14 shows another example of a device with a microfluidics channel network configuration.

FIG. 14 shows another example of a microfluidics channel network configuration. In some cases, a network configuration 1400 and constituents thereof may correspond to other network configurations (e.g., 800A, 800B, 900, 1000, 1100, 1200, 1300) described herein, and constituents thereof. In some cases, a droplet generating channel structure 1410 of the network configuration 1400 may correspond to other droplet generating channel structures described herein, such as the microfluidic channel structure 300, or other microfluidic channels structures described herein, such as with respect to FIGS. 1-6.

Each of a first channel segment 1401a and a second channel segment 1401b may source a partitioning fluid from the same partitioning fluid well and direct the partitioning fluid along the respective channels to a partitioning junction. A third channel segment 1402 may source a first input fluid from a first input fluid well and direct the first input fluid along the third channel segment to or in proximity to the partitioning junction. A fourth channel segment 1403 may source a second input fluid from a second input fluid well and direct the second input fluid along the fourth channel segment to or in proximity to the partitioning junction. In some instances, the first input fluid may be an aqueous fluid comprising one or more reagents. In some instances, the second input fluid may be an aqueous fluid comprising one or more particles, such as cell beads. In some instances, the cell beads may have a size of about 45 μm. As seen in the droplet generating channel structure 1410, the second input fluid may merge with the first input fluid upstream of the partitioning junction, and the merged fluid comprising the first and second input fluids may be merged with the partitioning fluids at the partitioning junction to generate one or more partitions. The emulsion products (e.g., droplets in partitioning fluid) may be directed away from the partitioning junction along an outlet channel segment 1404.

Provided are exemplary dimensions for the network configuration 1400 for use with 45 μm cell beads, such as for swelling chemistry applications that are described elsewhere herein. The first and second channel segments 1401a, b may have the same, or substantially the same lengths. In some instances, each of the first and second channel segments may have a cross-section dimension of about 72 μm. In some instances, the third channel segment 1402 may comprise a first segment upstream and a second segment downstream. The first segment may transition to the second segment gradually (e.g., via tapering) or abruptly. The first segment and second segment may be continuous. The first segment and the second segment may be in fluid communication. The first segment can have a length of about 16 mm, and a cross-section dimension of about 200 μm. The second segment may comprise a length of about 0.95 mm and a cross-section dimension of about 32 μm. The dimensions of the third channel segment 1402 may apply to the fourth channel segment 1403. Compared to earlier network configurations (and dimensions) described herein, the network configuration 1400 and the instant dimensions may allow for lower resistance (e.g., 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, or more times lower resistance) in the flow of aqueous fluid inputs and higher resistance (e.g., 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, or more times higher resistance) in the flow of partitioning fluid (e.g., oil) inputs. Beneficially, the wider and deeper channel segments carrying the aqueous fluid input (e.g., 1402, 1403) may allow for better priming of polymer solutions.

In another embodiment, provided are exemplary dimensions for the network configuration 1400 for use with 54 μm cell beads, such as for non-swelling chemistry applications that are described elsewhere herein. The first and second channel segments 1401a, b may have the same, or substantially the same lengths. In some instances, each of the first and second channel segments may have a cross-section dimension of about 72 μm at an upstream length of the segments (e.g., from about 25 to about 26 mm) which tapers to a cross-section dimension of about 38 μm at a downstream length of the segments (e.g., about 1 mm) immediately upstream of the partitioning junction. In some instances, the third channel segment 1402 may comprise a first segment upstream and a second segment downstream. The first segment may transition to the second segment gradually (e.g., via tapering) or abruptly. The first segment and second segment may be continuous. The first segment and the second segment may be in fluid communication. The first segment can have a length of about 15 to about 16 mm, and a cross-section dimension of about 200 μm. The second segment may comprise a length of about 1 mm to about 2 mm (e.g., 1.92 mm) and a cross-section dimension of about 38 μm. The dimensions of the third channel segment 1402 may apply to the fourth channel segment 1403. Compared to earlier network configurations (and dimensions) described herein, the network configuration 1400 and the instant dimensions may allow for lower resistance (e.g., 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, or more times lower resistance) in the flow of aqueous fluid inputs and higher resistance (e.g., 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, or more times higher resistance) in the flow of partitioning fluid (e.g., oil) inputs. Beneficially, the wider and deeper channel segments carrying the aqueous fluid input (e.g., 1402, 1403) may allow for better priming of polymer solutions.

As will be appreciated, the network configuration 1400 and/or droplet generating structure 1410 may be adjusted accordingly to generate droplets comprising different volumes, and/or different aqueous:partitioning fluid ratios. In some instances, a channel segment of the microfluidics channel and/or networks described herein may have a cross-section dimension from about 50 µm to about 200 µm. Alternatively in addition, a channel segment can have a cross-section dimension from at least about 50, 55, 65, 70, 75, 80, 85, 90, 95, 100, 105, 110, 115, 120, 130, 140, 150, 160, 170, 180, 190, 200 µm or more. Alternatively or in addition, a channel segment can be at most about 200, 190, 180, 170, 160, 150, 140, 130, 120, 115, 110, 105, 100, 95, 90, 85, 80, 75, 70, 65, 55, 50 µm or less.

Methods for Manufacturing Devices

The microfluidic devices, networks, and device modules of the present disclosure may be fabricated in any of a variety of conventional ways. For example, in some cases the devices comprise layered structures, where a first layer includes a planar surface into which is disposed a series of channels or grooves that correspond to the channel network in the finished device. A second layer includes a planar surface on one side, and a series of reservoirs defined on the opposing surface, where the reservoirs communicate as passages through to the planar layer, such that when the planar surface of the second layer is mated with the planar surface of the first layer, the reservoirs defined in the second layer are positioned in fluid communication with the termini of the channel segments on the first layer. Alternatively, both the reservoirs and the connected channel structures may be fabricated into a single part, where the reservoirs are provided upon a first surface of the structure, with the apertures of the reservoirs extending through to the opposing surface of the structure. The channel network is fabricated as a series of grooves and features in this second surface. A thin laminating layer is then provided over the second surface to seal, and provide the final wall of the channel network, and the bottom surface of the reservoirs.

These layered structures may be fabricated in whole or in part from polymeric materials, such as polyethylene or polyethylene derivatives, such as cyclic olefin copolymers (COC), polymethylmethacrylate (PMMA), polydimethylsiloxane (PDMS), polycarbonate, polystyrene, polypropylene, or the like, or they may be fabricated in whole or in part from inorganic materials, such as silicon, or other silica based materials, e.g., glass, quartz, fused silica, borosilicate glass, or the like.

Polymeric device components may be fabricated using any of a number of processes including embossing techniques, micromachining, e.g., laser machining, or in some aspects injection molding of the layer components that include the defined channel structures as well as other structures, e.g., reservoirs, integrated functional components, etc. In some aspects, the structure comprising the reservoirs and channel structures may be fabricated using, e.g., injection molding techniques to produce polymeric structures. In such cases, a laminating layer may be adhered to the molded structured part through readily available methods, including thermal lamination, solvent based lamination, sonic welding, or the like. For example, the devices of FIGS. 7-14 may be formed by injection molding.

As will be appreciated, structures comprised of inorganic materials also may be fabricated using known techniques. For example, channels and other structures may be micromachined into surfaces or etched into the surfaces using standard photolithographic techniques. In some aspects, the microfluidic devices or components thereof may be fabricated using three-dimensional printing techniques to fabricate the channel or other structures of the devices and/or their discrete components.

Computer Systems

Figure 16:
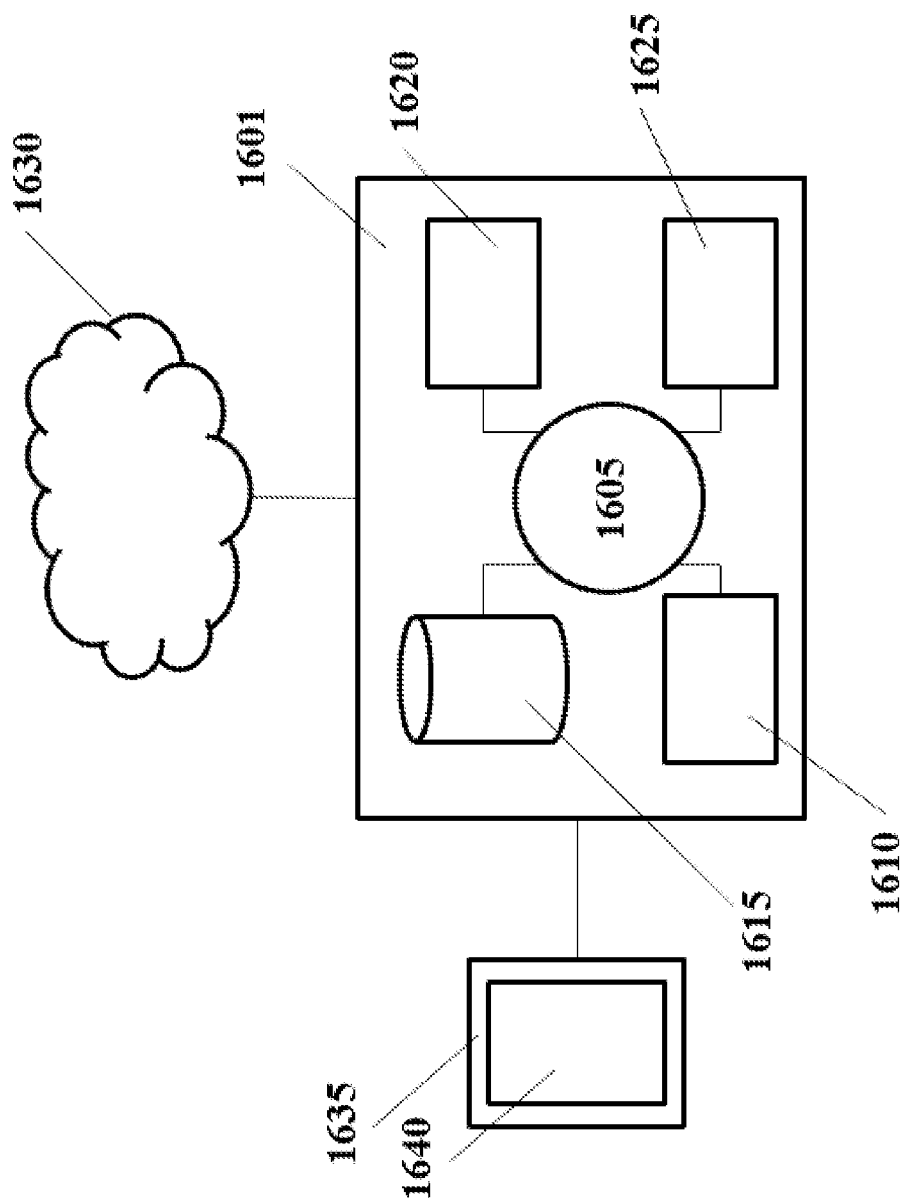
FIG. 16 shows a computer system that is programmed or otherwise configured to implement methods provided herein.

The present disclosure provides computer systems that are programmed to implement methods of the disclosure. FIG. 16 shows a computer system 1601 that is programmed or otherwise configured to control a microfluidics system (e.g., fluid flow), and/or perform sequencing applications. The computer system 1601 can regulate various aspects of the present disclosure, such as, for example, regulating fluid flow rate in one or more channels in a microfluidic structure. The computer system 1601 can be an electronic device of a user or a computer system that is remotely located with respect to the electronic device. The electronic device can be a mobile electronic device.

The computer system 1601 includes a central processing unit (CPU, also "processor" and "computer processor" herein) 1605, which can be a single core or multi core processor, or a plurality of processors for parallel processing. The computer system 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The computer system 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the computer system 1601, can implement a peer-to-peer network, which may enable devices coupled to the computer system 1601 to behave as a client or a server.

The CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and writeback.

The CPU 1605 can be part of a circuit, such as an integrated circuit. One or more other components of the system 1601 can be included in the circuit. In some cases, the circuit is an application specific integrated circuit (ASIC).

The storage unit 1615 can store files, such as drivers, libraries and saved programs. The storage unit 1615 can store user data, e.g., user preferences and user programs. The computer system 1601 in some cases can include one or more additional data storage units that are external to the computer system 1601, such as located on a remote server that is in communication with the computer system 1601 through an intranet or the Internet.

The computer system 1601 can communicate with one or more remote computer systems through the network 1630. For instance, the computer system 1601 can communicate with a remote computer system of a user (e.g., operator).

Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1601 via the network 1630.

Methods as described herein can be implemented by way of machine (e.g., computer processor) executable code stored on an electronic storage location of the computer system 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1601 can include or be in communication with an electronic display 1635 that comprises a user interface (UI) 1640 for providing, for example, operating parameters (e.g., pressure, volume, completion rate, etc.) or status of a microfluidics system, results of droplet generation, and results of sequencing analysis. Examples of UIs include, without limitation, a graphical user interface (GUI) and web-based user interface. Methods and systems of the present disclosure can be implemented by way of one or more algorithms. An algorithm can be implemented by way of software upon execution by the central processing unit 1605.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) form a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for generating a plurality of droplets, comprising:
a fluid flow path comprising a first channel, a second channel, a third channel, a fourth channel fluidically connecting an output reservoir and a drainage reservoir, and an intersection of said first channel and said second channel;
at least one fluid flow unit that is configured to (i) subject a first fluid to flow along said first channel and a second fluid to flow along said second channel to said intersection, and (ii) subject a plurality of droplets to flow along said third channel to said output reservoir; and
a controller operatively coupled to said fluid flow unit, wherein said controller is configured to direct said at least one fluid flow unit to (i) subject said first fluid to flow along said first channel towards said intersection and (ii) said second fluid to flow along said second channel towards said intersection, to generate said plurality of droplets upon said first fluid coming in contact with said second fluid, which plurality of droplets is subjected to flow along said third channel to said output reservoir,
wherein said fourth channel is configured to permit an excess of said second fluid to be drained from said output reservoir to said drainage reservoir using at least a hydrostatic pressure differential between said output reservoir and said drainage reservoir.

2. The system of claim 1, wherein said first fluid comprises a plurality of particles.

3. The system of claim 2, wherein during use, said plurality of particles comprises a plurality of biological particles and/or a plurality of particles having coupled thereto a plurality of barcodes.

4. The system of claim 1, wherein said at least one fluid flow unit includes at least one pump that is configured to provide negative pressure.

5. The system of claim 1, wherein said at least one fluid flow unit includes at least one compressor that is configured to provide positive pressure.

6. The system of claim 1, wherein said at least one fluid flow unit includes an actuator.

7. The system of claim 1, further comprising a plurality of drainage reservoirs, including the drainage reservoir, fluidically connected to said output reservoir via a plurality of drainage channels, including the fourth channel.

8. The system of claim 1, wherein said plurality of droplets has a higher density than said second fluid.

9. The method of claim 8, wherein said fourth channel is located above a predetermined threshold level in said output reservoir.

10. The system of claim 1, wherein said plurality of droplets has a lower density than said second fluid.

* * * * *